United States Patent
Cully et al.

(10) Patent No.: US 9,375,215 B2
(45) Date of Patent: Jun. 28, 2016

(54) DEVICE FOR RAPID REPAIR OF BODY CONDUITS

(75) Inventors: Edward H. Cully, Flagstaff, AZ (US); Jeffrey B. Duncan, Flagstaff, AZ (US); Keith M. Flury, Flagstaff, AZ (US); Paul D. Goodman, Flagstaff, AZ (US); Wayne D. House, Flagstaff, AZ (US); Vrad W. Levering, Flagstaff, AZ (US); Philip P. Off, Flagstaff, AZ (US); Daniel M. O'Shea, Stirling (GB); Michael J. Vonesh, Flagstaff, AZ (US); Jason M. Wiersdorf, Flagstaff, AZ (US)

(73) Assignee: W. L. GORE & ASSOCIATES, INC., Newark, DE (US)

( * ) Notice: Subject to any disclaimer, the term of this patent is extended or adjusted under 35 U.S.C. 154(b) by 0 days.

(21) Appl. No.: 11/624,513

(22) Filed: Jan. 18, 2007

(65) Prior Publication Data

US 2007/0198077 A1 Aug. 23, 2007

Related U.S. Application Data

(60) Provisional application No. 60/760,594, filed on Jan. 20, 2006.

(51) Int. Cl.
*A61F 2/94* (2013.01)
*A61B 17/11* (2006.01)
(Continued)

(52) U.S. Cl.
CPC . *A61B 17/11* (2013.01); *A61F 2/07* (2013.01); *A61F 2/97* (2013.01); *A61B 17/06166* (2013.01);
(Continued)

(58) Field of Classification Search
CPC .............. A61F 2/07; A61F 2/97; A61F 2/92; A61F 2/95; A61F 2250/0071; A61F 2220/0075; A61B 2017/1107
USPC ...................... 623/1.13, 1.12, 1.11
See application file for complete search history.

(56) References Cited

U.S. PATENT DOCUMENTS

| 567,962 A | 9/1896 | Cooper |
| 589,216 A | 8/1897 | McKee |

(Continued)

FOREIGN PATENT DOCUMENTS

| DE | 10104806 | 8/2002 |
| EP | 1192906 | 4/2002 |

(Continued)

OTHER PUBLICATIONS

Assadian A, Senekowitsch C, Rotter R, Zolss C, Strassegger J, Hagmuller G.W. Long-Term results of covered stent repari of internal carotid artery dissections. Journal of Vascular Surgery 2004;v 40 n 3:484-487.

(Continued)

*Primary Examiner* — Julie A Szpira

(57) ABSTRACT

A self-expanding stent-graft provided in a diametrically compacted state for implantation and retained preferably by a constraining sheath, useful for the temporary or permanent repair of injured, partially or entirely transected body conduits including blood vessels. It may be used under direct visualization to quickly stop or substantially reduce loss of blood from such damaged vessels and to quickly re-establish perfusion distal to the injury site. The device would typically be implanted under emergency room conditions but also be used in field situations by trained medical technicians. After an end of the device is inserted into a blood vessel through the injury access, deployment preferably initiates from the device end in a direction moving toward the middle of the length of the device by directionally releasing the constraining sheath. In a preferred embodiment, the two opposing ends of the device are individually deployable from the compacted, small diameter intended for insertion into a vessel, to the larger diameter at which they fit interferably into a portion of the vessel.

8 Claims, 26 Drawing Sheets

(51) Int. Cl.
*A61F 2/07* (2013.01)
*A61F 2/97* (2013.01)
*A61B 17/06* (2006.01)
*A61F 2/06* (2013.01)
*A61F 2/30* (2006.01)
*A61F 2/89* (2013.01)

(52) U.S. Cl.
CPC ......... *A61B 2017/1107* (2013.01); *A61F 2/064* (2013.01); *A61F 2/89* (2013.01); *A61F 2002/075* (2013.01); *A61F 2002/30713* (2013.01); *A61F 2220/0075* (2013.01); *A61F 2220/0091* (2013.01); *A61F 2250/0087* (2013.01)

(56) References Cited

U.S. PATENT DOCUMENTS

| | | |
|---|---|---|
| 1,151,300 A | 8/1915 | Soresi |
| 1,470,707 A | 10/1923 | Bates |
| 2,453,056 A | 11/1948 | Zack |
| 2,836,181 A | 5/1958 | Tapp |
| 3,221,746 A | 12/1965 | Noble |
| 3,435,824 A | 4/1969 | Gamponia |
| 3,435,826 A | 4/1969 | Fogarty |
| 3,516,408 A | 6/1970 | Montanti |
| 3,657,744 A | 4/1972 | Ersek |
| 3,683,926 A | 8/1972 | Suzuki |
| 4,721,109 A | 1/1988 | Healey |
| 4,728,328 A | 3/1988 | Hughes et al. |
| 4,753,236 A | 6/1988 | Healey |
| 5,201,757 A * | 4/1993 | Heyn et al. ............... 606/198 |
| 5,330,490 A | 7/1994 | Wilk et al. |
| 5,389,087 A | 2/1995 | Miraki |
| 5,405,378 A | 4/1995 | Strecker |
| 5,409,469 A | 4/1995 | Schaerf |
| 5,522,881 A * | 6/1996 | Lentz ............... 623/1.13 |
| 5,534,007 A | 7/1996 | Germain et al. |
| 5,591,195 A | 1/1997 | Taheri et al. |
| 5,591,226 A | 1/1997 | Trerotola et al. |
| 5,662,703 A | 9/1997 | Yurek et al. |
| 5,674,241 A | 10/1997 | Bley et al. |
| 5,725,570 A | 3/1998 | Heath |
| 5,747,128 A | 5/1998 | Campbell et al. |
| 5,755,769 A | 5/1998 | Richard et al. |
| 5,755,775 A | 5/1998 | Trerotola et al. |
| 5,755,778 A | 5/1998 | Kleshinski |
| 5,788,707 A | 8/1998 | Del Toro et al. |
| 5,800,506 A | 9/1998 | Perouse |
| 5,921,995 A | 7/1999 | Kleshinski |
| 6,019,788 A | 2/2000 | Butters et al. |
| 6,143,022 A | 11/2000 | Shull et al. |
| 6,168,623 B1 | 1/2001 | Fogarty et al. |
| 6,179,878 B1 | 1/2001 | Duerig et al. |
| 6,224,627 B1 | 5/2001 | Armstrong et al. |
| 6,235,051 B1 | 5/2001 | Murphy |
| 6,283,992 B1 | 9/2001 | Hankh et al. |
| 6,315,792 B1 * | 11/2001 | Armstrong et al. .......... 623/1.23 |
| 6,334,867 B1 | 1/2002 | Anson |
| 6,344,054 B1 | 2/2002 | Parodi |
| 6,352,561 B1 * | 3/2002 | Leopold et al. ............. 623/1.23 |
| 6,371,979 B1 | 4/2002 | Beyar et al. |
| 6,387,118 B1 | 5/2002 | Hanson |
| 6,497,722 B1 | 12/2002 | Von Oepen et al. |
| 6,558,396 B1 * | 5/2003 | Inoue ............... 606/108 |
| 6,629,992 B2 | 10/2003 | Bigus et al. |
| 6,645,239 B1 | 11/2003 | Park et al. |
| 6,733,473 B1 | 5/2004 | Reifart et al. |
| 6,733,521 B2 | 5/2004 | Chobotov et al. |
| 6,827,731 B2 | 12/2004 | Armstrong et al. |
| 6,899,727 B2 | 5/2005 | Armstrong et al. |
| 6,942,682 B2 | 9/2005 | Vrba et al. |
| 6,945,990 B2 | 9/2005 | Greenan |
| 6,955,688 B2 | 10/2005 | Wilson et al. |
| 6,966,887 B1 | 11/2005 | Chin |
| 7,722,665 B2 | 5/2010 | Anwar |
| 8,123,797 B2 | 2/2012 | Anwar |
| 8,282,680 B2 | 10/2012 | Kao et al. |
| 2002/0004663 A1 | 1/2002 | Gittings et al. |
| 2002/0087176 A1 | 7/2002 | Greenhalgh |
| 2002/0107535 A1 | 8/2002 | Wei et al. |
| 2002/0143381 A1 | 10/2002 | Gilligan et al. |
| 2004/0073282 A1 | 4/2004 | Stanish |
| 2005/0107862 A1 | 5/2005 | Ohlenschlaeger |
| 2005/0215938 A1 | 9/2005 | Khan et al. |
| 2006/0015171 A1 * | 1/2006 | Armstrong ............... 623/1.12 |
| 2007/0027526 A1 | 2/2007 | Demetriades et al. |
| 2010/0191322 A1 | 7/2010 | Anwar |

FOREIGN PATENT DOCUMENTS

| | | |
|---|---|---|
| FR | 2768921 | 4/1999 |
| JP | 2003-245343 | 9/2003 |
| WO | 84/03036 | 8/1984 |
| WO | 96/39999 | 12/1996 |
| WO | 9819631 | 5/1998 |
| WO | 98/27894 | 7/1998 |
| WO | 9827893 | 7/1998 |
| WO | 99/65420 | 12/1999 |
| WO | 02/15823 | 2/2002 |
| WO | 03/082152 | 10/2003 |
| WO | 03103513 | 12/2003 |
| WO | 2006102020 | 9/2006 |

OTHER PUBLICATIONS

Battaglia L, Bartolucci R, Minucci S, Biancari F, Rabitti G. Stent Graft Repair for Rupture of the Subclavian Artery Secondary to Infection of a Subclavian-to-Carotid Bypass Graft. Ann Vasc Surg 2001; 15:474-476.
Bedi V, Bhargav S, Dahl A. Use of the Hemobahn Endoprosthesis for Trauma in a Military Hospital. W.L. Gore & Associates, Inc. brochure. Jan. 2000.
Burger T, Halloul Z, Meyer F, Grote R, Lippert H. Emergency Stent-Graft Repair of a Ruptured Hepatic Artery Secondary to Local Postoperative Peritonitis. J Endovasc Ther 200; 7:324-327.
Demetriades D, Chahwan S, Gomez H, Pent R, Velmahos G, Murray J, Asensio J, Bongard F. Penetrating Injuries to the Subclavian and Axillary Vessels. J Am Coll Surg 1999; v 188 n 3: 290-295.
Du Toit DF, Strauss DC, Blaszczyk M, de Villiers R, Warren BL. Endovascular Treatment of Penetrating Thoracic Outlet Arterial Injuries. European Journal of Vascular 7 Endovascular Surgery 2000;19:489-495.
Fox C, Gillespie D, O'Donnell S, Rasmussen T, Goff J, Johnson C, Galagon R, Sarac T, Rich N. Contemporary management of wartime vascular trauma. J Vasc Surg 2005; 41:638-44.
Gerasimidis T, Sfyroeras G, Papazoglou K, Trellopoulos G, Ntinas A, Karamanos D. Endovascular Treatment of Popliteal Artery Aneurysms. Eur J Vasc Endovasc Surg 2003; 26:506-511.
Gil S, de Espana F, Irurzun J, de la Iglesia P, Verdu J. Endoluminal treatment of traumatic arteriovenous fistulae with Hemobahn covered stents. Cardio Vascluar and Interventional Radiology 2003; 26 (Supplement 1).
Gil S, de Espana F, Irurzun J, de la Iglesia P, Verdu J. Percutaneous Treatment of iatrogenic arterial lesions with e-PTFE covered stents. CIRSE 2004; Abstract P85, p. 198.
Hossny A. Blunt popliteal artery injury with complete lower limb ischemia: Is routine use of temporary intraluminal arterial shunt justified? Journal of Vascular Surgery 2004; v 40 n. 1: 61-66.
Ihlberg L, Roth W, Alback N, Kantonen I, Lepantalo M. Successful percutaneous endovascular treatment of a ruptured popliteal artery aneyrysm. J Vasc Surg 200; 31:794-7.
Kumar V. Endovascular treatment of penetrating injury of axillary vein with Viabahn endoprosthesis. Journal of Vascular Surgery 2004; 40: 1243-4.
McArthur C, Marin M. Endovascular Therapy for the Treatment of Arterial Trauma. The Mount Sinai Journal of Medicine 2004; v 71 n1:4-11.
McCarthy S, Marin M, Veith F, Bakal C, Kvetan V. Endovascular Stented Graft Repair of a Pseudoaneurysm of the Subclavian Artery

(56) References Cited

OTHER PUBLICATIONS

Caused by Percutaneous Internal Jugular Vein Cannulation: Case Report. American Journal of Critical Care 1995; v4 n6:472-475.

Oktar G, Balkan M, Akpek S, Ilgit E. Endovascular Stent-Graft Placement for the Management of a Traumatic Axillary Artery Pseudoaneurysm: A Case Report. Vasc Endovascular Surg 2002; vol. 36(4):323-326.

Patel A, Marin M, Veith F, Kerr A, Sanchez L. Endovascular Graft Repair of Penetrating Subclavian Artery Injuries. J Endovasc Surg 1996; 3:382-388.

Rosa P, O'Donnell S, Goff J, Gillespie D, Starnes B. Endovascular Management of a Peroneal Artery Injury Due to a Military Fragment Wound. Ann Vasc Surg 2003; 17:678-681.

Schoder M, Cejna M, Holzenbein, Bischof G, Lomoschitz F, Funovics M, Nobauer-Huhmann I, Sulzbacher I, Lammer J. Elective and emergent endovascular treatment of subclavian artery aneurysms and injuries. Journal of Endovascular Therapy 2003;10 (1):58-65.

Synovis. Flo-Thru Intraluminal Shunt Brochure. 1998.

Verhelst H, Lauwers G, Schroe H. Endovascular Treatment of Trauma of the Subclavian Artery with the Hemobahn Endoprosthesis. May 2000.

Vermassen F, Deroose J. Covered Stents in Non-Stenotic, Non-Aneurysmal Arterial Lesions. European Summer Symposium. Jun. 25-27, 1998. Brussels, Belgium.

Vinces F, Sperling D. Endovascular treatment of a combined pseudoaneurysm and arteriovenous fistula of the subclavian artery caused by a gunshot wound to the chest. J Thorac Cardiovasc Surg 2005; 130:225-7.

Xenos E, Freeman M, Stevens S, Cassada D, Pacanowski J, Goldman M. Covered stents for injuries of subclavian and axillary arteries. Journal of Vascular Surgery 2003; 451-454.

Zanchetta M, Rigatelli G, Dimopoulos K, Pedon L, Zennao M, Maiolino P. Endoluminal repair of axillary artery and vein rupture after reduction of shoulder dislocation. Minerva Cardioangiol 2002; 50(1):69-73.

* cited by examiner

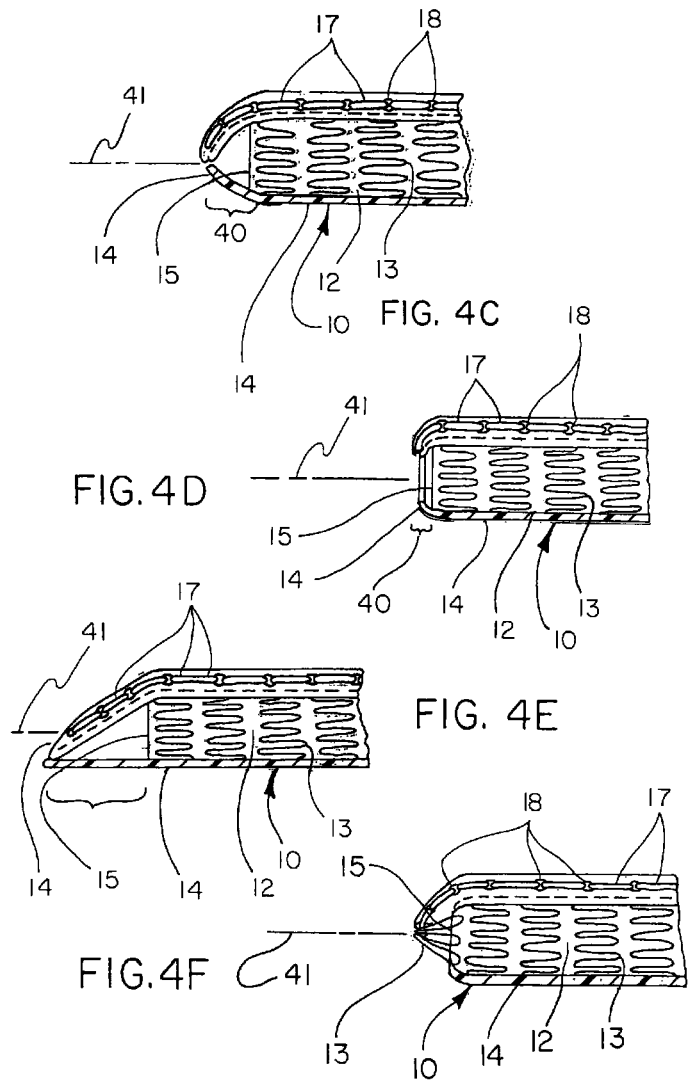

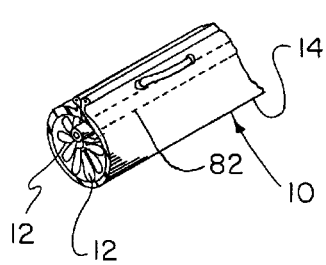 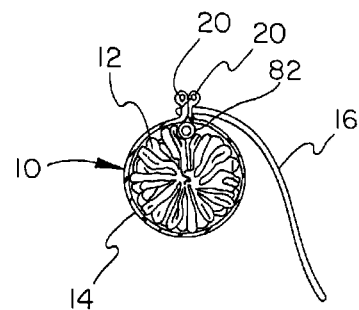
FIG. 8A  FIG. 8B
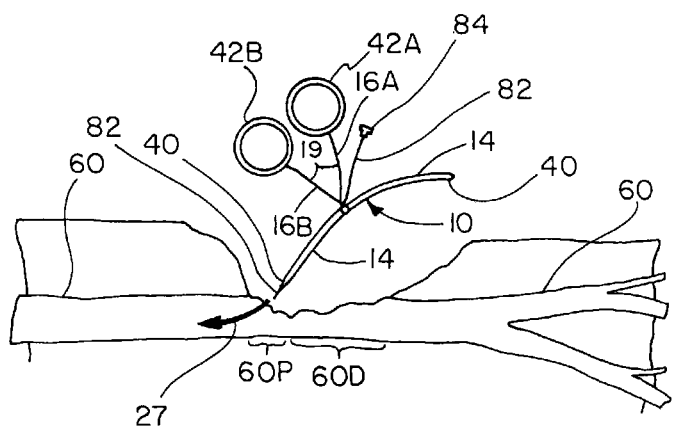
FIG. 8C

DEVICE FOR RAPID REPAIR OF BODY CONDUITS

CROSS REFERENCE TO RELATED APPLICATIONS

This application claims the benefit of U.S. Provisional Patent Application No. 60/760,594, filed on Jan. 20, 2006

FIELD OF THE INVENTION

The present invention relates to the field of medical devices useful in the repair of trauma to body conduits, particularly to an implantable device useful for such repairs, and more particularly to a self-expanding stent-graft useful for such repairs.

BACKGROUND OF THE INVENTION

Injuries to body conduits, particularly to the vascular system, are commonplace. These injuries are frequently life-threatening, exsanguination often occurring as a result of such injuries. Blood vessels may be lacerated or may be completely transected, including incidents involving amputations of limbs. The use of endoprostheses such as stent-grafts to temporarily or permanently repair such injuries offers the potential to considerably reduce the loss of blood and risk of loss of life. These devices may be quickly implanted under direct visualization at the site of such injuries, halting or substantially reducing loss of blood and maintaining perfusion of an affected limb. This may be accomplished during emergency room procedures and may also be possible at the site of an accident by qualified emergency personnel.

Implantation of endoprostheses including stent-grafts under direct visualization at the site of surgically-created traumas is known. U.S. Pat. No. 3,657,744 to Ersek describes the implantation of a bifurcated vascular graft into a surgically-created transection of the aorta wherein the graft ends are secured within the blood vessel by individually deployed balloon expanded stents.

Similarly, U.S. Pat. Nos. 5,591,226 and 5,755,775 to Trerotola et al. teach the use of non-bifurcated stent-grafts for the repair of transected blood vessels under direct visualization wherein cannula devices ("vascular access means") are first inserted into each of the exposed, transected ends of the blood vessel. The two ends of the self-expanding stent-graft are retained in a compacted small diameter by individual, longitudinally splittable retaining sheaths. The small compacted diameter of the stent-graft allows for individual insertion of the ends of the device into the cannula devices within the exposed ends of the transected vessel. After insertion into the ends of the blood vessel, each end of the stent-graft is separately deployed from its initial, compacted diameter to its larger, final diameter by longitudinal splitting of the cannula devices and the retaining sheaths; these components are simultaneously removed from the transected end of the blood vessel while they are being longitudinally split. The splitting of the retaining sheath is accomplished beginning from the end of the sheath closest to the middle of the length of the stent-graft and proceeding toward the end of the stent-graft, thereby allowing the stent-graft to deploy to its larger, full diameter in the same direction as the splitting of the retaining sheath. Causing the deployment of the stent-graft to occur from the middle toward the ends is undesirable as the ends of the graft may be pushed out of the ends of the blood vessel as the diameter of the stent-graft increased in that direction.

U.S. Pat. No. 6,019,788 to Butters et al. describes an arteriovenous shunt graft having y-shaped ends that are insertable under direct visualization into transected blood vessels and deployable from the smaller diameter at which they were inserted to a larger diameter that secures them with the transected ends of the blood vessel. U.S. Pat. Nos. 5,755,778 and 5,921,995 to Kleshinski teach tubular stent-grafts for use as anastomotic devices that are inserted into transected ends of blood vessels and deployed.

Percutaneously inserted stent-grafts have also been used for the repair of traumatic injuries. For example, a paper by Dr. Vinay Kumar ("Endovascular treatment of penetrating injury of axillary vein with Viabahn endoprosthesis," Journal of Vascular Surgery, December 2004, pp. 1243-1244) describes repairing a knife wound of an axillary vein by delivering the endoprosthesis to the injured site via the basilic vein. Deployment of the device at the injury site resulted in immediate control of hemorrhage.

WO99/65420 describes a restraining cover for retaining a self-expandable endoprosthesis in its compacted, small diameter state prior to deployment. The cover has opposing ends that are separately releasable (allowing separate deployment of the two opposing ends of the contained endoprosthesis), with deployment of the individual ends of the contained endoprosthesis initiated by the application of tension to separate rip cords that release from the center of the length of the cover. WO98/27894 teaches a stent-graft that is deployable beginning from the middle of the length of the device and progressing simultaneously toward both ends.

U.S. Pat. No. 3,221,746 to Noble teaches the use of an anastomotic connector useful for the repair of severed tubular canal members, regardless of whether the severing is the result of accident, illness or surgery. U.S. Pat. No. 4,721,109 to Healey describes a temporary anastomotic device for maintaining blood flow in damaged blood vessels. Greenhalgh, in US Patent Application Publication 2002/0087176 discusses a tubular support intended as an anastomosis device for veins and arteries, the device comprising a tubular braided structure of elastic filamentary fibers optionally including an elastomeric membrane covering over the tubular braided structure.

These various devices of the prior art have thus far been unsuccessful in the field of emergency repair of body conduits. There remains a need for a quickly-effective device that reduces the risk of loss of substantial amounts of blood and the associated risk of loss of limb or life.

SUMMARY OF THE INVENTION

The present invention relates to medical devices useful in the repair of accidental or intentional trauma to body conduits (e.g., blood vessels), particularly to endoprostheses useful for such repairs, and more particularly to self-expanding stent-grafts useful for such repairs. The stent-graft of the present invention is useful for the repair of partially or entirely transected body conduits such as blood vessels. The device serves as an implantable self-expanding shunt. It may be used to quickly stop or substantially reduce loss of blood from such damaged vessels and to quickly re-establish perfusion distal to the trauma site. While intended primarily for the repair of accident-induced trauma, these devices may also be used to accomplish surgical repairs that are not the result of accidents.

A stent-graft is considered herein to be a stent component typically comprising a metal frame having a generally tubular shape and provided with a covering of biocompatible graft material over surfaces of the stent component that covers spaces between adjacent elements of the stent component.

The metal is preferably nitinol and may be nitinol wire that has preferably been electropolished. The graft covering may be provided over the inner surface of the stent component, or over the outer surface of the stent component, or over both the inner and outer surfaces of the stent component. While the stent covering most typically extends along the entire length of the stent component, alternatively the stent component may extend beyond the graft covering at either or both ends of the device.

The term endoprosthesis is used herein to describe an implantable device that has a small compacted diameter for insertion into a body conduit and a subsequent larger diameter to which it is deployed when situated at the desired location in the body conduit. For many anticipated applications, only a portion of the length of the endoprosthesis may be inserted into and deployed within a portion of a body conduit while another portion may remain outside of the body conduit when used as described herein; i.e., it is not required that the entire length of the endoprosthesis is inserted into a body conduit.

While primarily self-expanding endoprostheses are described herein, it is apparent that such devices that are also balloon expandable may be useful. For example, following implantation of an endoprosthesis, it may be desirable to subsequently use a catheter balloon to slightly increase the diameter of the implanted device. Such self-expanding, balloon adjustable devices are known; see, for example, U.S. Pat. No. 6,336,937.

The device (or constrained endoprosthesis assembly) of the present invention is intended as a temporary repair or permanent (definitive) repair for situations requiring prompt intervention in order to reduce the risk of loss of life or limb. It will typically be manually implanted under direct visualization at an exposed site. Manual implantation involves the direct use of a practitioners hand and may include the use of tools such as hemostats, forceps, etc. The device may be used as a temporary repair, for example, in use for 96 hours or less, due to potential complications such as the risk of infection at an accidental trauma site. A subsequent permanent repair can be effected (by, for example, conventional vascular surgical techniques or by replacing the initially implanted device with another similar or equivalent device) at a later time when the patient is stabilized and at reduced risk of infection. However, it is appreciated that under suitable circumstances the device may preferably be left implanted as a definitive, permanent repair.

While it is anticipated that the device would be implanted under typical emergency room conditions, it might also be used in field situations by trained paramedics or military medics.

As implanted, the device creates effective sutureless anastomosis between the endoprosthesis and the body conduit. Stay sutures may optionally be used, however.

The constrained endoprosthesis assemblies may also be provided in bifurcated form.

The device is created without requirement for any holes or punctures through any portion of the wall of the graft material covering the stent that could result in loss of contained liquid such as blood. The optional use of stay sutures may result in temporary bleeding through any resulting suture holes made through the wall of the device. This type of bleeding is typically quickly resolved through conventional vascular surgery techniques. For stent-grafts made with the stent elements provided on the exterior of the stent-graft, the device may also be sutured without creating holes through the wall of the device. This is accomplished by suturing under the wire elements of the stent without puncturing the wall of the graft material.

In a preferred embodiment, the two opposing ends of the device (each preferably extending to about the mid-length portion of the device) are individually deployable from the compacted, small diameter intended for insertion into a vessel, to the larger diameter at which they fit interferably into a portion of the vessel and provide an open conduit for passage of blood with little or no leakage. Also preferably, deployment initiates from the device end in a direction moving toward the middle of the length of the device, with each end of the device being individually and independently deployable. The opposing ends may optionally be deployed simultaneously if desired. The device is self-expanding, being contained within one or more constraining sheaths to hold the device at its compacted, small diameter prior to deployment. Each constraining sheath is preferably formed from a thin sheet of strong, flexible and biocompatible material wrapped about the compacted small diameter of the self expanding device with two opposing edges of the sheet secured together temporarily to form a tubular constraint about the device. When two constraining sheaths are provided, they individually constrain opposing ends of the device and each preferably extends to about the middle of the length of the device, although the two sheaths may constrain portions of the graft that differ in length. In another alternative, the two sheaths together may constrain only a portion of the graft length leaving a center portion unconstrained. Further, in another embodiment, the two constrained end portions of the assembly may be of different lengths.

While, as noted above, it is preferred that deployment occurs beginning from the end of the device and progressing toward the middle, it is possible to create devices that deploy in the opposite direction or that deploy simultaneously along the constrained length.

The constraining sheath may take several forms. It may be a sheet of biocompatible material wrapped in cigarette-fashion (with longitudinally oriented adjacent sheet edges) about the exterior surface of the compacted endoprosthesis, with the adjacent edges of the wrapped sheet secured together in a quickly releasable manner. It may alternatively take the form of an unravelable tubular knit. Another form is an unravelable strand structure bound about the outside of the compacted endoprosthesis, an example of which is taught by U.S. Pat. No. 5,405,378 to Strecker. Additionally, the use of corrugations may be provided on any surface of the constraining sheath. For example, an everted portion may not be corrugated while an underlying portion may be corrugated. Of course, any combination of corrugated and non-corrugated portions may be used. Corrugations may be uniform, non-uniform, or combinations of the two throughout the length of the constraining sheath.

When a sheet of material is used to make a constraining sheath that wraps in a tubular fashion about the outer surface of the constrained endoprosthesis, it may be secured about the circumference of the compacted device by, for example, a coupling member such as a filament arranged so as to form a longitudinally oriented stitch that holds the opposing, longitudinally oriented edges of the constraining sheath together in adjacent relationship. The stitch is analogous to releasable stitches used, for example, as a closure for feed bags (e.g., an unravelable chain stitch arranged as a series of loops or slip knots, such as a single thread type 101 chain stitch). When tension is applied to one end of such a stitch, the securing stitch is released sequentially beginning from one end of the device and progressing toward the middle portion of the device, thereby progressively releasing the constraining sheath and allowing that end of the self-expanding device to deploy to its larger diameter. The constraining sheath may be implantable and remain in vivo as long as the device is left in place, or alternatively may be removable during or after deployment of the device. The implantable constraining sheath is optionally attached to the endoprosthesis by any suitable method such as one or more stitches on the side of the endoprosthesis diametrically opposite the joined sheath edges, these optional stitches securing the sheath to the stent component. A single constraining sheath may be used to constrain the full length of the device, with two different length portions of the constraining sheath having separate coupling members to allow release of the constraint thereby allowing separate deployment of the different length portions of the device. Thus the application of tension to only one of the two coupling members releases the constraint at one end of the device when the practitioner is ready to deploy that end of the device without affecting the opposite end.

The edges of the constraining sheath may alternatively be configured in the fashion of a piano hinge whereby the coupling member is a filament or wire that, analogous to a hinge pin, secures the opposing edges of the constraining sheath together. Device deployment is initiated by applying tension to the coupling member to cause it to slide axially out of the piano-hinged edges of the constraining sheath, allowing these edges to part and release the constrained self-expanding device as will be further described.

In another preferred embodiment, the constrained endoprosthesis assembly is provided with tapered tips (or end portions) serving as introducers that make it easier to introduce the ends of the device into a damaged vessel. The pointed tip portion is preferably created as the tip or end portion of the constraining sheath, with this tip portion of the constraining sheath extending beyond the end of the constrained endoprosthesis. The constraining sheath in this embodiment is preferably removable following deployment of the endoprosthesis. Removal of the constraining sheath following deployment may be accomplished by gripping the exposed portion of the constraining sheath with forceps and applying axial tension, thereby causing the constraining sheath to slide axially out of its location between the outer surface of the deployed endoprosthesis and the luminal surface of the body conduit. Optionally, a portion of the constraining sheath near the middle of the device length may be provided with a handle to better enable removability.

The device may also be provided with an introducer component (i.e., an axial stiffening component) that may optionally be incorporated into the constraining sheath or simply incorporated between the sheath and endoprosthesis to stiffen the device for introduction into one end of a damaged vessel and to also provide a relatively pointed tip to one end of the device. In another embodiment, an axial stiffening component may be incorporated within the lumen of the device. After the first end of the device has been successfully introduced into a trauma site, the stiffening component may be withdrawn by the application of tension to an exposed and accessible end of the stiffening component, in a direction away from the first end of the device.

These axial stiffening components may be provided with variable stiffness along their length if desired.

In still another alternative, two separate devices may be used to effect the desired repair, particularly in the case of a fully transected vessel. According to a preferred method of using two devices, one end of a first device is inserted and deployed into the proximal end of the transected vessel while one end of a second device is inserted and deployed into the distal end of the transected vessel. The opposing end of either device is deployed (preferably the distal device) and the opposing end of the other device is inserted into that deployed end for a suitable length (typically 2 cm to 5 cm) and deployed.

The deployed diameter of the device must fit interferably within the lumen of the vessel at the repair site in order to minimize any leakage between the two. It is preferred that the deployed diameter of the device should be about 5 to 100% larger than the inside diameter of the vessel into which the device is intended to be fitted. More preferably, it should be about 5 to 20% larger. It may be as much as 150% larger, however, this much interference risks damage to the vessel and creates a risk of folds, particularly longitudinally oriented folds, occurring in the device when it is deployed. Typically, about 1 cm to about 5 cm of the length of the device is inserted into the damaged vessel lumen prior to deployment to minimize risk of leakage, with about 3 cm being preferred. For fully transected vessels, it is anticipated that an additional device length of approximately 3-6 cm may be useful to compensate for typical retraction of the ends of the transected vessel.

Preferred endoprostheses are Hemobahn® Endoprosthesis and Viabahn® Endoprosthesis available from W.L. Gore & Associates, Flagstaff Ariz. These devices include a self-expanding stent in the form of a helical winding of serpentine nitinol wire provided with a porous expanded polytetrafluoroethylene (hereinafter ePTFE) graft covering within the stent component. The stent design allows for the device to grip the luminal surface of the vessel, with minimal leakage. They may be secured to adjacent tissue (temporarily or permanently) by passing a suture between the stent component and the adjacent graft component without penetrating through the graft component. These devices may also be subsequently removed from the vessels in which they were previously deployed by the application of tension to the device. 5 to 20 cm long devices of this type may be used, for example, with 6 and 8 mm deployed diameters being deemed to be suitable for most vascular applications. It is apparent that a wide range of lengths and diameters may be useful.

The constrained endoprosthesis may also be coated entirely or in part with any desired therapeutic agent such as, for example, heparin. The use of an ePTFE tubular graft for that portion of the assembly is particularly effective in this regard due to the microporous nature of that material that may be used to advantage as a reservoir for therapeutic agents. More than one therapeutic agent may be used in combination. For example, the outer surface of the graft may be provided with a coating of an antimicrobial such as silver chlorhexidene while a heparin coating may be bonded to the luminal surface.

BRIEF DESCRIPTION OF THE DRAWINGS

FIGS. 4C-4F are partial longitudinal cross sectional views of constraining sheaths with alternative tapered ends.

FIG. 7A shows a hybrid stent-graft and vascular graft of the present invention, while

FIGS. 8A-8C are respectively a perspective view including a transverse cross section, a transverse cross sectional view and an application schematic showing the optional use of an axial stiffening component (a length of hypotube) with the constrained endoprosthesis assembly of the present invention.

DETAILED DESCRIPTION OF THE DRAWINGS

Figure 1A:
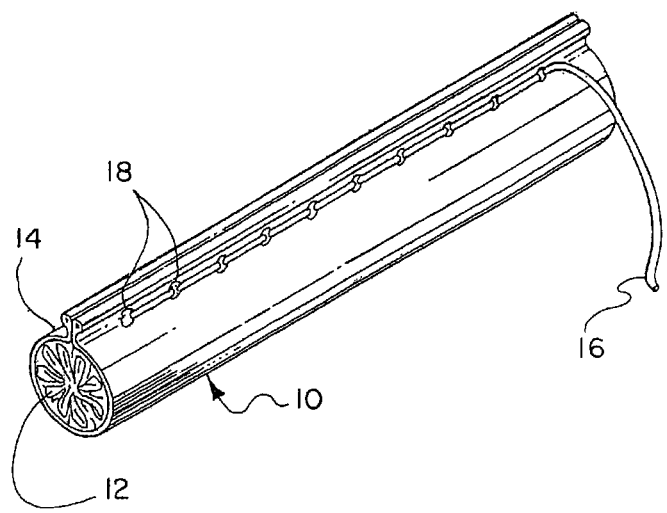
FIGS. 1A and 1B show respectively a perspective view and an end view of a self-expanding endoprosthesis contained within a releasable constraining sheath, according to the prior art.
Figure 1B:
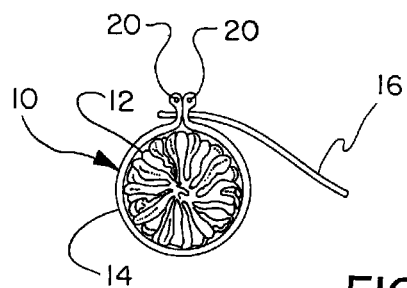

FIG. 1A shows a perspective view of a constrained endoprosthesis assembly 10, generally as known in the prior art. FIG. 1B shows an end view of the same assembly 10. The assembly 10 as shown is described in further detail by WO 98/27894. The endoprosthesis 12 is typically a self-expanding stent-graft, i.e., a self-expanding stent 13 provided with a tubular covering 15 of a prosthetic graft material (e.g., porous expanded polytetrafluoroethylene, or ePTFE) that enables the endoprosthesis 12 to convey and contain a fluid such as blood between its ends without loss. The covering graft material 15 may be provided on the inner surface of the stent 13, or the outer surface of the stent 13, or both the inner and outer surfaces of the stent 13 with the stent consequently encapsulated between inner and outer graft coverings 15.

The constrained endoprosthesis assembly 10 is shown compacted to a small diameter to enable its practical insertion into a body conduit (e.g., the vasculature). The self-expanding endoprosthesis 12 is retained in the compacted, small diameter state by constraining sheath 14, typically a sheet of biocompatible material (e.g., ePTFE) wrapped around the compacted endoprosthesis 12 to create a tubular form useful for maintaining the endoprosthesis 12 in its small diameter constrained state. The adjacent edges of the constraining sheath 14 are secured together with a coupling member such as a filament 16, arranged in an unravelable chain stitch sewn through a series of perforations 18 in the adjacent edges of the constraining sheath 14, to allow for convenient release of the constrained endoprosthesis 12 in order to enable its deployment to a larger diameter at a desired location in vivo (e.g., in the vasculature). The edges of the constraining sheath 14 may be optionally reinforced if desired, for example with an embedded filament 20 such as a length of ePTFE suture material.

Figure 1C:
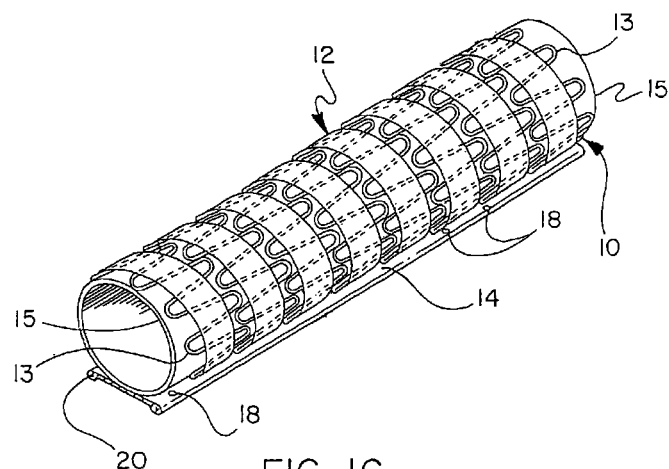
FIGS. 1C and 1D show respectively a perspective view and an end view of the self-expanding endoprosthesis of FIGS. 1A and 1B deployed following release from within the constraining sheath, according to the prior art.
Figure 1D:
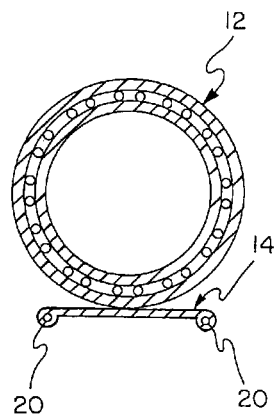

FIGS. 1C and 1D are respectively perspective and end views of the endoprosthesis assembly 10 following release of the constraining sheath 14 such as by the application of tension to the end of the coupling member (filament) 16. Endoprosthesis 12 is shown at its fully expanded diameter as it would appear in a deployed state at a desired in vivo location. Constraining sheath 14 is fully released from its previous tubular form and remains adjacent one side of deployed endoprosthesis 12. The constraining sheath 14 of the present invention may optionally be secured to one side of endoprosthesis 12 along the line of contact shown in FIGS. 1C and 1D by various methods such as sutures through the constraining sheath 14 attached to stent 13, preferably without penetrating the graft covering 15, if it is desired to leave the constraining sheath 14 in vivo with endoprosthesis 12. Alternatively, sheath 14 may be left unsecured to endoprosthesis 12 if it is intended that sheath 14 be removable following deployment of endoprosthesis 12.

Figure 1E:
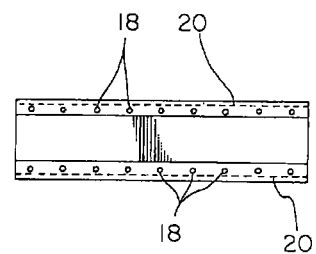
FIG. 1E shows a plan view of the constraining sheath of FIGS. 1C and 1D as it appears following release of the contained endoprosthesis.

FIG. 1E shows a plan view of constraining sheath 14.

Figure 1F:
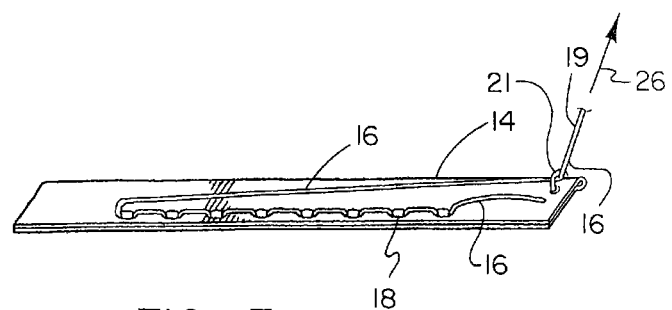
FIGS. 1F, 1G and 1H show details of an unravelable chain stitch that allows release of the constraining sheath and deployment of the endoprosthesis by the application of tension to one end of a filament that makes up the unravelable chain stitch.
Figure 1G:
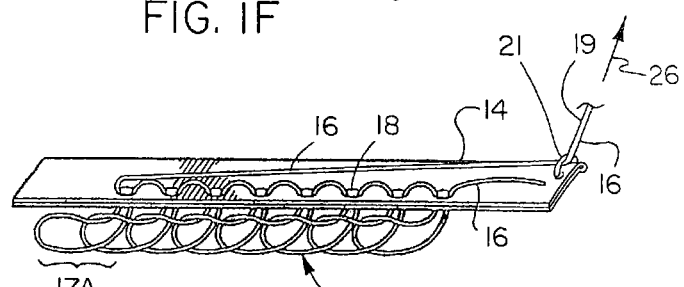
Figure 1H:
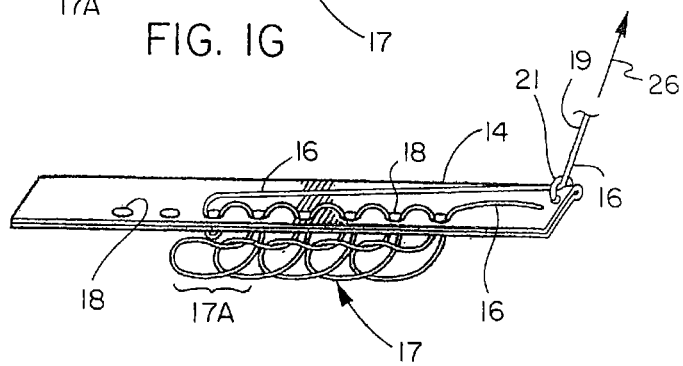

FIGS. 1F, 1G and 1H show details of an unravelable chain stitch 17 useful with endoprostheses contained in a compacted state by the use of a constraining sheath 14 (such as shown in FIGS. 1A and 1B) that allows release of the constraining sheath 14 and deployment of the endoprosthesis 12 by the application of tension to one end 19 of a filament 16 that makes up the chain stitch. These figures describe one slip knot configuration for an unravelable chain stitch 17 that may be used in conjunction with the filamentary or thread-like coupling member 16. Constraining sheath 14 is shown without an implant positioned therein for purposes of simplification. FIG. 1F illustrates the slip knot in a prerelease or predeployment state. The series of knots generally add very little profile (thickness). FIG. 1G shows the assembly of FIG. 1F with the thread-like coupling member 16 loosened to illustrate how the chain knots 17A may be formed. FIG. 1H diagrammatically represents release of the assembly of FIG. 1F or 1G. The illustrated stitch 17 is releasable by pulling one end 19 of the coupling member 16 that results in releasing of the tubular constraining member 14 and then deployment of the endoprosthesis 12 (not shown). This particular stitch is a type of unravelable chain stitch 17 and may be created with a single needle and a single filament, resulting in a series of loops or slip knots 17A that are looped through one another such that one slip knot prevents the next slip knot from releasing. When the filament 16 is pulled to release a slip knot 17A, the following slip knot is then released and that in turn releases the next slip knot. This process continues during pulling of the filament 16 until the entire filament is pulled out of the constraining member 14.

Referring to FIGS. 1F-1H, as the end portion 19 of the thread-like coupling member 16 is pulled, such as in the direction shown by reference arrow 26, each consecutive chain knot 17 releases the next adjacent chain knot. Chain knots 17 of the coupling member 16 are preferably arranged to progressively release the collapsed endoprosthesis 12 (not shown) in a direction away from the end portion of the endoprosthesis 12 toward the middle portion of the length of the endoprosthesis 12 by the use of a securing loop 21. Unlike the chain stitch release orientation shown in FIGS. 1A and 1B, FIGS. 1F-1H show how filament 16 is routed back away from the end of the assembly 10 intended to be initially released, back to securing loop 21 located typically near the middle of the length of the assembly 10. Securing loop 21 also enables a ninety degree change in direction of filament 16 in order that tension may be applied to end 19 of filament 16 in a direction substantially perpendicular to the length of assembly 10 as will be discussed in further detail.

Figure 1J:
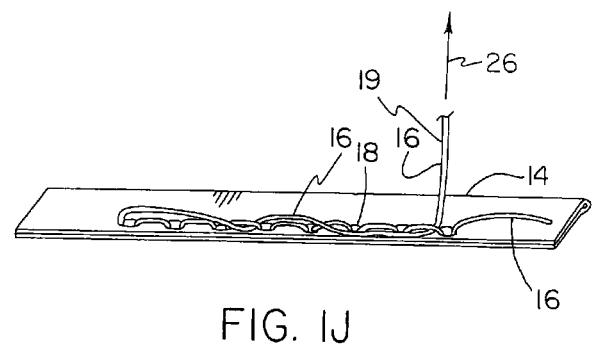
FIGS. 1J, 1K and 1L show details of an unravelable chain stitch incorporating an alternative routing of the filament to which tension is applied to effect unraveling of the chain stitch.
Figure 1K:
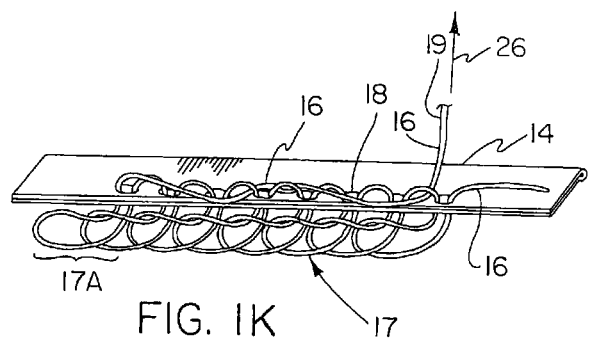
Figure 1L:
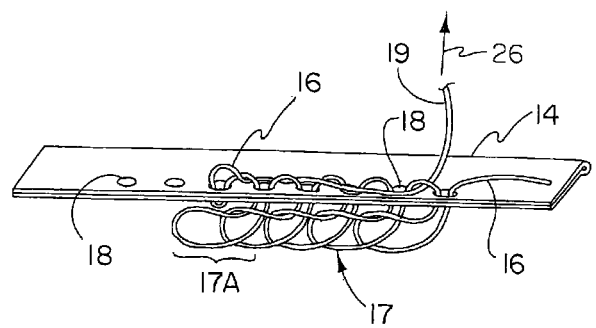

If assembly 10 is sufficiently flexible that the possibility of "bowstringing" of filament 16 during deployment may be a concern, one or more additional securing loops may be used between the end and middle portions of the assembly. Alternatively, filament 16 may be routed at intervals under one or more chain stitch loops as shown in FIGS. 1J-1L.

Figure 2:
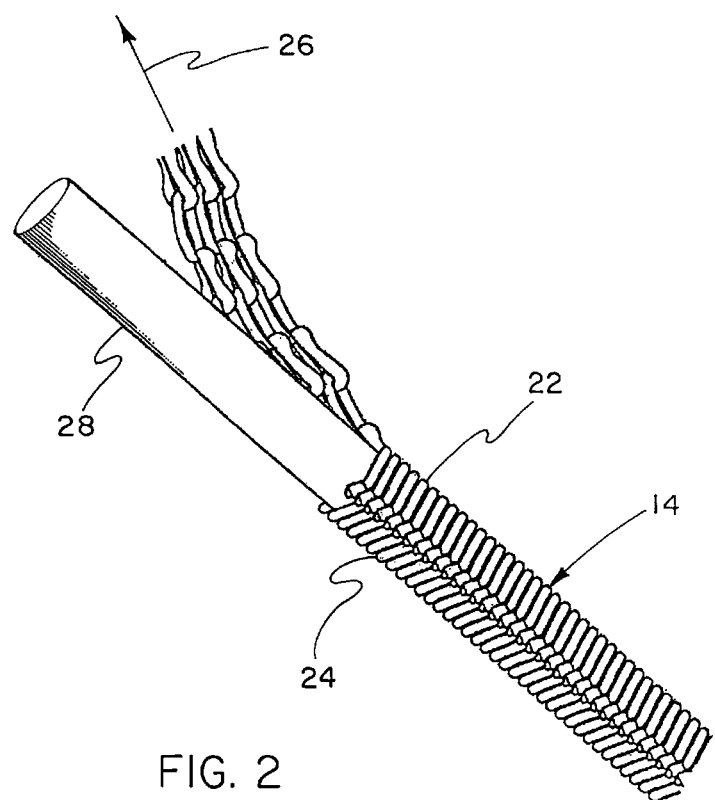
FIG. 2 shows a perspective view of an alternative constraining sheath made from a knitted tubular construction according to the prior art.

FIG. 2 shows a perspective view of an alternative constraining sheath 14 made from a knitted tubular construction according to the prior art. In this instance, the sheath 14 is unravelable, as described in detail in U.S. Pat. No. 6,224,627 to Armstrong et al. The embodiment shown is a four fiber 22, 24 warp knit (or knit-braid) construction. The application of tension as shown by arrow 26 to the four fibers at the end of the constraining sheath 14 causes the knitted tubular construction to unravel and thereby expose an underlying cylindrical device, shown as mandrel 28 for clarity although it is apparent that the cylindrical device may be a self-expanding endoprosthesis that is deployed as a result of releasing a constraining force by unraveling of sheath 14.

Figure 3A:
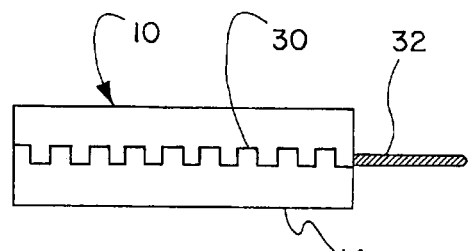
FIGS. 3A-3C show views of an alternative constraining sheath incorporating a piano hinge according to the prior art.
Figure 3B:
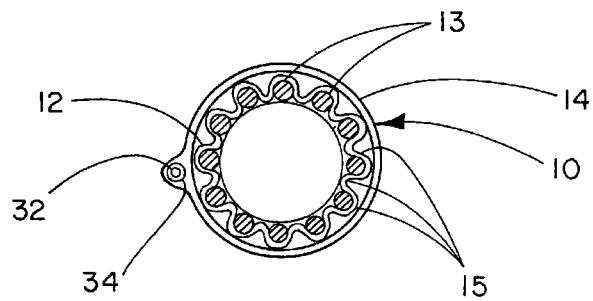
Figure 3C:
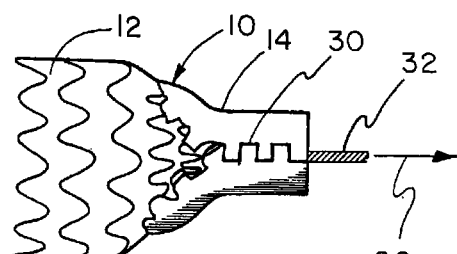

FIGS. 3A-3C show views of an alternative constraining sheath incorporating a piano hinge according to the prior art; constraining sheaths of this type are further described by U.S. Pat. No. 6,827,731 to Armstrong et al. FIG. 3A is a plan view of a constrained endoprosthesis assembly 10 incorporating a constraining sheath 14 utilizing a piano hinge closure 30 wherein the edges of the constraining sheath 14 are secured together via a hinge pin component 32 that is axially removable by the application of tension. This release is shown in progress in the plan view of FIG. 3C wherein tension is being applied to hinge pin component 32 in direction 26 causing progressive release of constraining sheath 14 thereby allowing deployment of the self-expanding endoprosthesis 12.

Hinge closure 30 may optionally incorporate a length of relatively small diameter polymeric tubing 34 shown in the transverse cross section of FIG. 3B. The incorporation of a length of such tubing 34 is a convenient way to deal with the edges of the material comprising constraining sheath 14. Alternatively, the material of the constraining sheath 14 may be sufficient without such a length of tubing if simply formed to create a passageway for the hinge pin component 32.

It is apparent that two separate hinge pin components 32 may be used whereby each one releases one end of the constrained endoprosthesis 12. These may be set up so that the exposed end to which tension is to be applied extends outwardly away from the constrained endoprosthesis assembly 10 near the middle of the length of the assembly. In this way, each end of the assembly may be separately and individually deployable.

It is apparent that there are numerous ways that a suitable constraining sheath 14 may be created to enable containment of a compacted endoprosthesis 12 and to allow its controlled release and deployment when desired. In particular, many (if not all) of these various constraining sheath constructions may be configured to allow for separate and individual deployment of the two opposing ends of the endoprosthesis as is preferred for the present invention. Methods of compacting self-expanding endoprostheses to their smallest practical diameter for delivery into a patient are known, as are various methods of capturing the compacted endoprosthesis within a suitable constraining sheath. One such method of compacting the endoprosthesis involves the use of a device such as described in U.S. Pat. No. 6,702,845. The compacted endoprosthesis is then slid temporarily from the compacting device into a length of a relatively thinwall polymeric tubing that is of greater length than the length of the endoprosthesis. The constraining sheath of desired length (also less than the length of the temporary polymeric tubing) is then fitted tightly around the polymeric tubing, after which the polymeric tubing is slid out of the constraining sheath with the endoprosthesis blocked axially from moving from within the polymeric tubing by a length of mandrel (of smaller outside diameter than the outside diameter of the compacted endoprosthesis), thereby ensuring that the compacted endoprosthesis remains within the constraining sheath during and following removal of the temporary polymeric tubing.

Figure 4A:
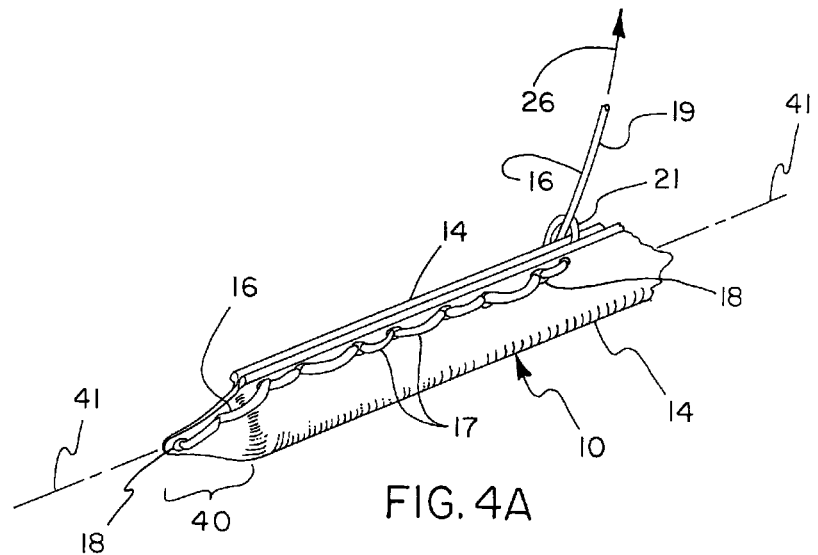
FIG. 4A shows a perspective view of one end of a constrained endoprosthesis of the present invention, wherein at least one end of the constraining sheath extends beyond the adjacent end of the constrained endoprosthesis with the extended end of the constraining sheath forming a pointed end of smaller diameter than the constrained endoprosthesis to facilitate introduction of the end of the assembly into a traumatized vessel.

FIG. 4A shows a perspective view of one end of a constrained endoprosthesis assembly 10 of the present invention, wherein at least one end of the constraining sheath 14 extends beyond the adjacent end of the constrained endoprosthesis with the extended end of the constraining sheath forming a point 40 of smaller diameter than the diameter of the constrained endoprosthesis to facilitate introduction of the end of the assembly into a traumatized vessel. A pointed tip thus has a smallest measurable diameter at its end that is at least 85% or less than that of the outside diameter of the constrained endoprosthesis assembly. More preferably, the smallest measurable diameter at the pointed tip is less than 80%, 75%, 70%, 65%, 60%, 55%, 50%, 45%, 40%, 35%, 30%, 25%, 20%, 15%, or even 10% of the outside diameter of the constrained endoprosthesis. Further, a line drawn parallel to the surface of the pointed portion will intersect the longitudinal axis 41 of the cylindrical assembly when the assembly is in a straight configuration, and will intersect another line through the surface of the constraining sheath portion that covers the endoprosthesis which latter line is parallel to the longitudinal axis 41 of the assembly.

There are a variety of ways to provide the constraining sheath with a pointed tip portion 40 extending beyond the end of the endoprosthesis, including various molding and shaping techniques known in the art of forming polymeric shapes. For a constraining sheath 14 made from porous expanded PTFE (ePTFE), this material may be densified to reduce or eliminate the porosity in the pointed tip portion 40 of the constraining sheath 14. This densification may be accomplished by the local application of heat to the ePTFE material in this tip region. The resulting substantial reduction or elimination of porosity causes the material to shrink, thereby reducing the dimensions of the material at the tip portion 40 and simultaneously increasing the stiffness of the material, also desirable for creation of a pointed introducer tip 40. The edges of this pointed tip portion 40 of the constraining sheath 14 may be sewn together with the releasable chain stitch continuously with the adjacent portion of the sheath 14 that constrains the endoprosthesis, so that when tension is applied to filament 16 at the end of the chain stitch, the releasing of the joined edges of the constraining sheath commences beginning at the pointed tip 40 and continuing away from the tip toward the middle of the length of the constrained endoprosthesis.

Figure 4B:
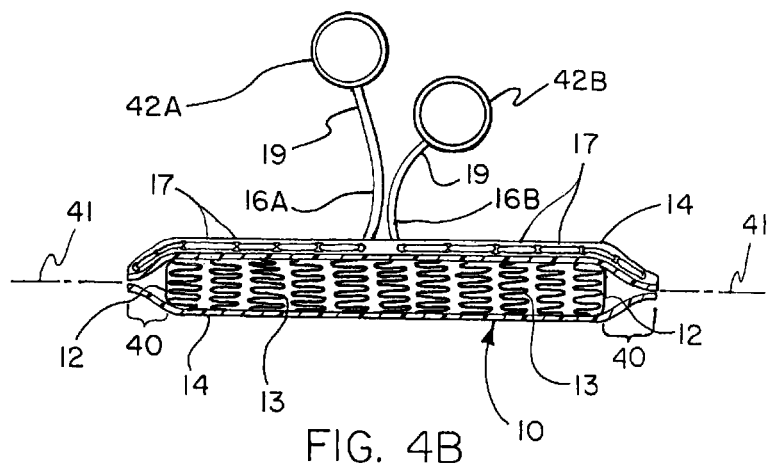
FIG. 4B shows a longitudinal cutaway view of the entire length of the assembly shown in FIG. 4A.

FIG. 4B is a longitudinal cutaway view of the entire length of the constrained endoprosthesis assembly 10 shown in FIG. 4A, wherein constraining sheath 14 is shown cutaway to provide a view of the constrained endoprosthesis 12. Pointed ends 40 formed in constraining sheath 14 extend beyond the ends of endoprosthesis 12. A pair of separate filaments 16A and 16B are arranged as unravelable chain stitches 17 to allow separate deployment of the two ends of assembly 10, with each filament 16 arranged to initiate deployment of the respective assembly end beginning from the end and progressing back toward the middle of the length of the assembly.

The ends 19 of each filament 16A and 16B are attached respectively to pull rings 42A and 42B. The use of these preferred pull rings provides a convenient grip for a practitioner to use in the application of each individual filament 16. It is further preferred that the pull rings be differently colored, with, for example, pull ring 42A and filament 16A colored the same, and pull ring 42B and filament 16B colored the same, but different from the color used for pull ring 42A and filament 16A. For example, pull ring 42A and filament 16A may be made to be black, while pull ring 42B and filament 16B may be made to be white. In this fashion, it will be apparent to the practitioner which pull ring deploys which end of the assembly. For further clarity, it may be desired to color the pointed ends of the constraining sheath the same as the respective pull ring and filament (using different colors for each of the two pointed ends). In another alternative, each entire constraining sheath end may be colored with different colors used for the two ends, again with the respective pull rings colored the same as the ends that they are intended to release.

It is apparent that the filaments 16 and pull rings 42 allow for the application of tension (to initiate deployment) at an angle of about 90 degrees with respect to the longitudinal axis 41 of assembly 10. The filaments and pull rings 42 are arranged so that tension may be applied over a wide range of angles with respect to the longitudinal axis 41, ranging from virtually parallel to the longitudinal axis 41 to 90 degrees and beyond.

FIGS. 4C-4F are partial longitudinal cross sectional views of constraining sheaths with alternative pointed ends. FIG. 4C shows an embodiment wherein constraining sheath 14 has a rounded point 40. As shown in FIG. 4D, the constraining sheath 14 may simply extend over and around the end of the endoprosthesis 12. FIG. 4E describes an embodiment wherein pointed tip is asymmetrical with one side being substantially parallel with the longitudinal axis 41 and the other side possessing most of the taper. It is apparent that either side of point 40 may possess most of the taper (e.g., the side including chain stitch 17). This embodiment may be particularly useful with an axial stiffening component as will be further described. FIG. 4F shows an embodiment wherein elements of stent 13 extend beyond the end of graft component 15; these extended ends are temporarily bent inward toward longitudinal centerline 41 and secured with the end of chain stitch 17 to create point 40. Following insertion of this end of the assembly 10 into the body conduit, the application of tension to filament 16 begins deployment by initiating unraveling of chain stitch 17 at the end of device 10, freeing the joined ends of stent 13 at the tip of point 40 and allowing the ends of the stent to open in alignment with the remainder of the body of the stent as it deploys.

Figure 5A:
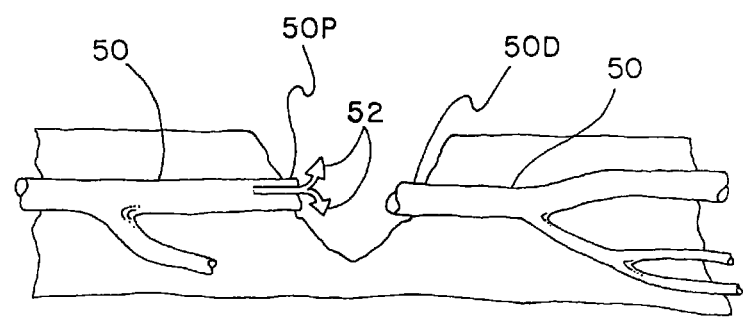
FIGS. 5A-5E show schematic representations of the assembly of the present invention being used to repair a transected artery.
Figure 5B:
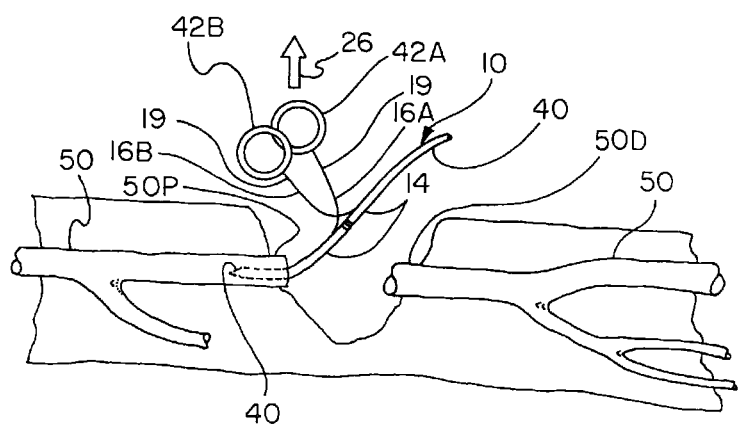

FIGS. 5A-5E show schematic representations of the device of the present invention being used to repair a transected artery 50. FIG. 5A describes the transected blood vessel, with arrows 52 indicating blood loss from the proximal side 50P of the transection. FIG. 5B shows one end of assembly 10 being inserted into the proximal side 50P of transected artery 50, preparatory to being deployed by the application of tension (indicated by arrow 26) to pull ring 42A and filament 16A. While this schematic shows adequate clearance between the lumen of the transected blood vessel and the outer diameter of the constrained endoprosthesis assembly, this may be a slip fit with a slight interference. In the case of transected blood vessels, the retraction of the vessel ends will often require that the vessel ends be gripped with forceps during insertion of one end of the assembly 10. A typical transection may require that 2 to (more preferably) 3 cm of insertion length of the end of the assembly prior to deployment of the end. Often a 5 cm length of endoprosthesis will be necessary between the retracted ends. Thus, a device length of about 11-12 cm may be desired. A desirable amount of diametrical interference in the deployed device would be about 30-50%. For example, for a 6 mm blood vessel, an endoprosthesis with a nominal deployed diameter of 8 mm may be desirable.

Figure 5C:
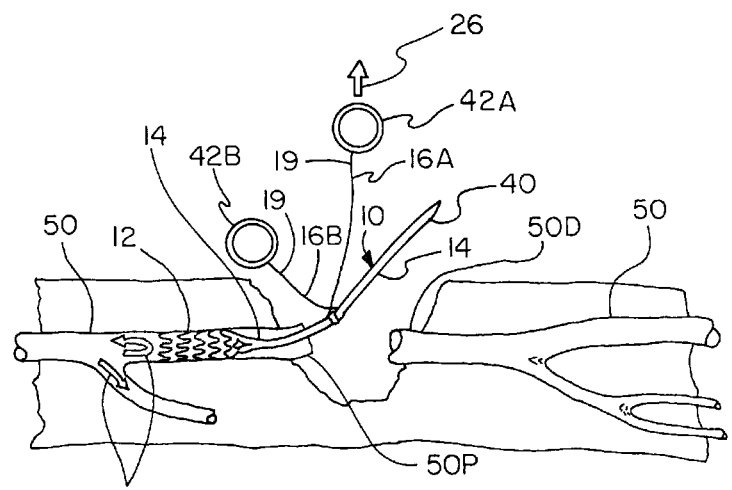

FIG. 5C shows the end of assembly 10 inserted into and deployed within the proximal side 50P of transected artery 50, deployment having occurred from the pointed tip 40 and proceeding toward the middle of the length of the assembly. As only this end of the assembly has been deployed, blood loss is substantially reduced or stopped entirely, with blood pressure largely re-established as shown by arrows 53. The opposing end of assembly 10, having not yet been deployed from its compacted state, serves to block blood flow. The released constraining sheath that had formerly constrained this end of the device is not shown, but is captured between the outer surface of a portion of the deployed device and the adjacent luminal surface of the proximal end of the artery. Optionally, this portion of the constraining sheath may be removed following deployment by the application of axial tension to the constraining sheath 14, if the constraining sheath 14 was not physically attached to the endoprosthesis. It is generally believed preferable to utilize an implantable constraining sheath and leave it in place between the deployed endoprosthesis and the vessel wall.

Figure 5D:
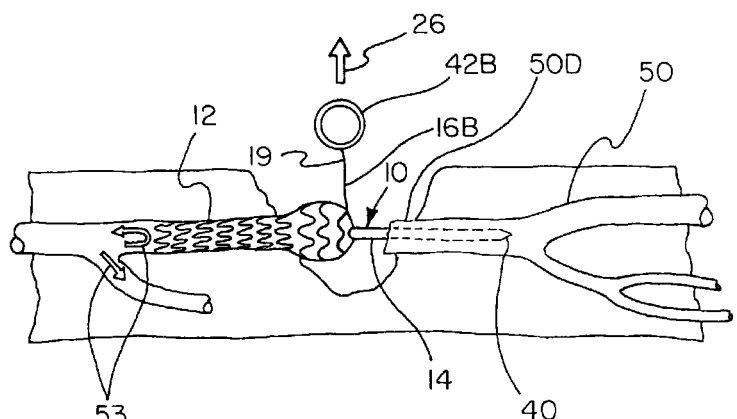
Figure 5E:
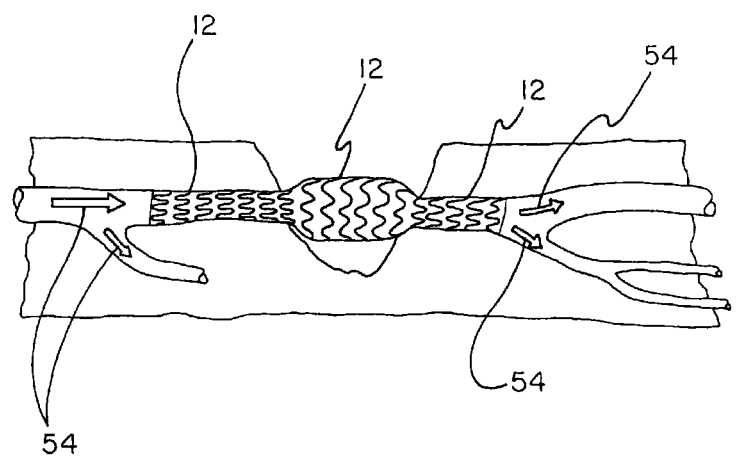

FIG. 5D shows the opposing end of assembly 10 inserted into the distal end 50D of artery 50, preparatory to deployment by the application of tension (indicated by arrow 26) to remaining pull ring 42B and filament 16B. FIG. 5E shows the deployment of the distal end having been accomplished, with perfusion re-established distally as indicated by arrows 54.

FIGS. 5A-5E describe one possible sequence of using the present invention to repair transected vessels. It is apparent that there are other possible sequences. For example, the device may be inserted into both the proximal and distal vessel ends and then be deployed at both ends simultaneously.

Figure 6A:
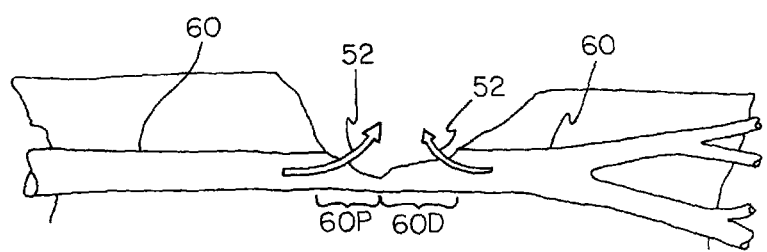
FIGS. 6A-6D show schematic representations of the assembly of the present invention being used to repair a trauma to a blood vessel wherein the wound is only partially through the vessel.

FIG. 6A is a schematic representation of a trauma to a blood vessel such as artery 60 wherein the wound is only partially through the vessel (i.e., the vessel is not fully transected).

Figure 6B:
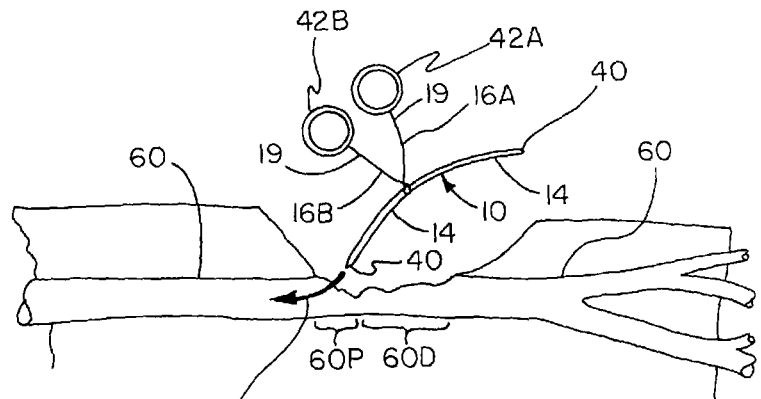
Figure 6C:
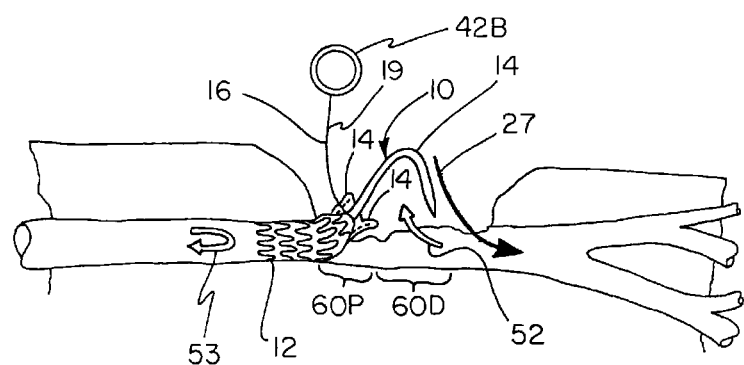

FIG. 6B is a schematic representation of the same wound further showing a constrained endoprosthesis assembly 10 of the present invention about to be inserted into the proximal side of the trauma site. FIG. 6C shows the assembly 10 fully inserted and deployed (by the application of tension to pull ring 42A of FIG. 6B) into the proximal side of the wound. As the distal end of the assembly 10 is as yet undeployed, the compacted distal portion of the endoprosthesis serves as a plug or occluder and prevents further blood loss; pressure is substantially restored (arrow 53). This distal portion of the assembly 10 is now bent appropriately to be directed into the distal portion 60D of the trauma site, as indicated by arrow 27.

Figure 6D:
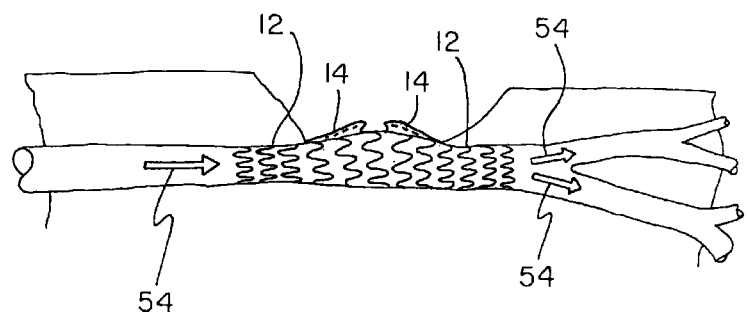

FIG. 6D shows the assembly 10 fully deployed with distal blood flow re-established (arrows 54) with little or no further loss of blood.

Figure 7A:
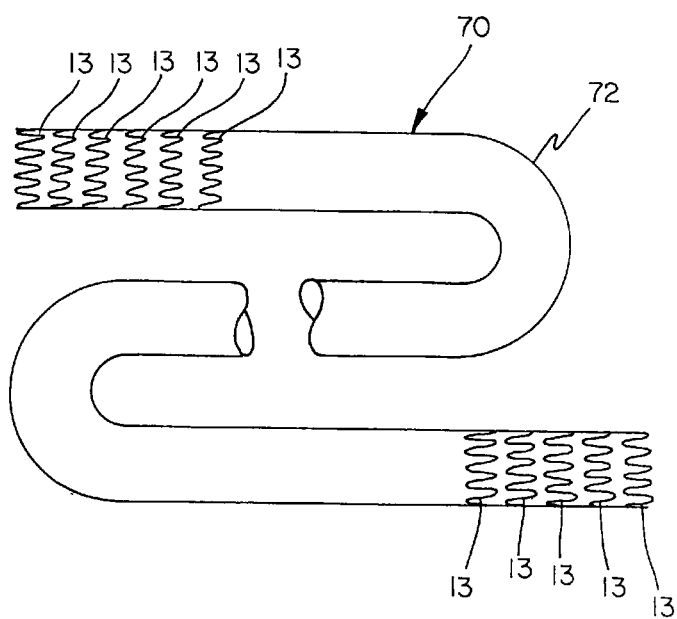
Figure 7B:
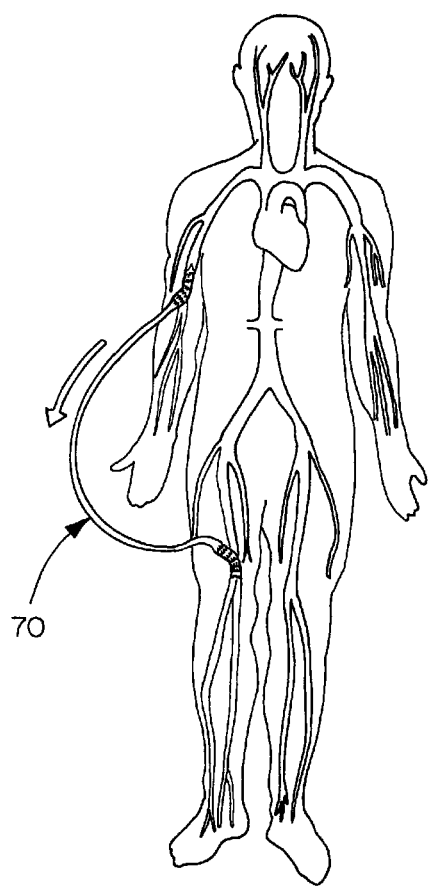
FIG. 7B shows an application of this hybrid device.

An alternative device is described in the plan view of FIG. 7A which shows that the endoprosthesis can be a hybrid stent-graft and vascular graft 72, having a stent component 13 adapted to the exterior surface, or alternatively to the interior surface, of both ends of a vascular graft 72 such as an ePTFE vascular graft. The same type of constraining sheath described above can be used independently at each end of the graft (constraining sheath not shown in this view). Such a hybrid device can be used to advantage to perfuse a trauma site from an entirely different location in the body, as shown by FIG. 7B.

The assembly of the present invention may optionally be provided with various components intended to add axial stiffness to the assembly to further facilitate introduction into an opening in a blood vessel. These axial stiffening components are removable once the introduction has been accomplished as desired. Such components include hypotubes and guidewires or rod components referred to herein as guide mandrels. They may optionally extend beyond the tip of the assembly.

FIG. 8A is a perspective view terminating in a transverse cross section showing a length of a small tubular component such as a hypotube 82 fitted within the constrained endoprosthesis assembly 10. FIG. 8B is an end cross sectional view of assembly 10 fitted with a hypotube as a stiffening component 82. The hypotube 82 resides between the endoprosthesis 12 and the constraining sheath 14. Its diameter, wall thickness and material are chosen for the appropriate degree of stiffness that is chosen to be added to the assembly 10. An appropriate nitinol hypotube is part no. SE508 from Nitinol Devices and Components, Fremont Calif. The assembly 10 needs sufficient flexibility to be adequately conformable to the anatomy both during and following implantation. However, the additional axial stiffness imparted by a stiffening component such as hypotube 82 can be useful during the process of inserting the tip 40 of the assembly into an opening in a traumatized blood vessel. It is possible to add an appropriate stiffening component without excessively compromising flexibility in the assembly.

The use of a hollow hypotube as an axial stiffening component 82 offers the possibility of also allowing for a convenient access for local administration of a therapeutic agent. Likewise, the use of a hollow hypotube allows for the possible use of a guidewire device if desired to better enable access to the damaged vasculature. A hypotube can also serve as a channel for a deployment filament.

FIG. 8C is a side schematic view of a constrained endoprosthesis assembly 10 preparatory to implantation at a vascular trauma site. This view shows how the axial stiffening component, in this instance a length of hypotube 82, may extend away from the assembly near the middle portion of the length of the assembly, typically at the same location that the filament segments 16A and 16B extend away from the assembly 10 to join their respective pull rings 42A and 42B. A suitable handle or optional luer access fitting 84 may be fitted to this end of stiffening component 82. Once the assembly is inserted into the vasculature for the desired distance, stiffener 82 may be removed by pulling it away from assembly 10 while assembly 10 is firmly held in place by the practitioner. Stiffener may be removed prior to or following deployment of that end of endoprosthesis 12. Alternatively, it may be left in place for local drug delivery access or guidewire access.

FIG. 8C also indicates how the opposite end of stiffener 82 may extend beyond the tip portion 40 of the assembly 10. This may be desirable to provide particular stiffness at the very end of the assembly 10 and as such may aid in locating and entering the vascular opening. The stiffener 82 is suitably formed to offset at tip portion 40 so that it terminates at the center of the pointed tip portion 40.

Figure 9A:
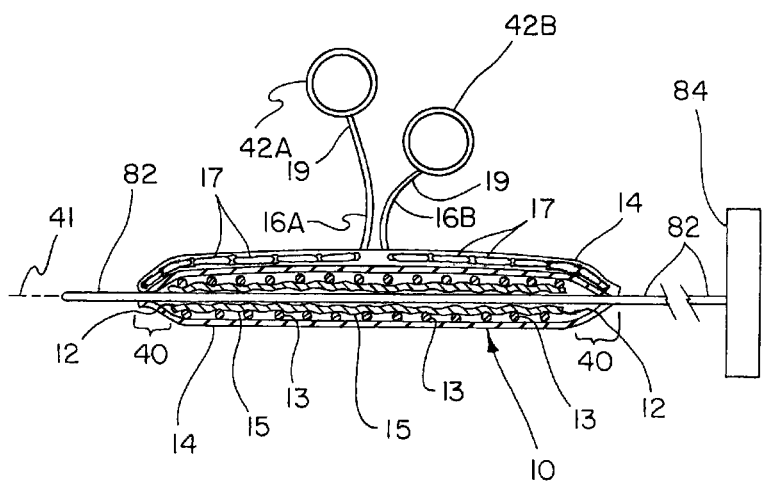
FIGS. 9A-9C are side views of an embodiment incorporating an axial stiffener that extends for the full length of the device.
Figure 9B:
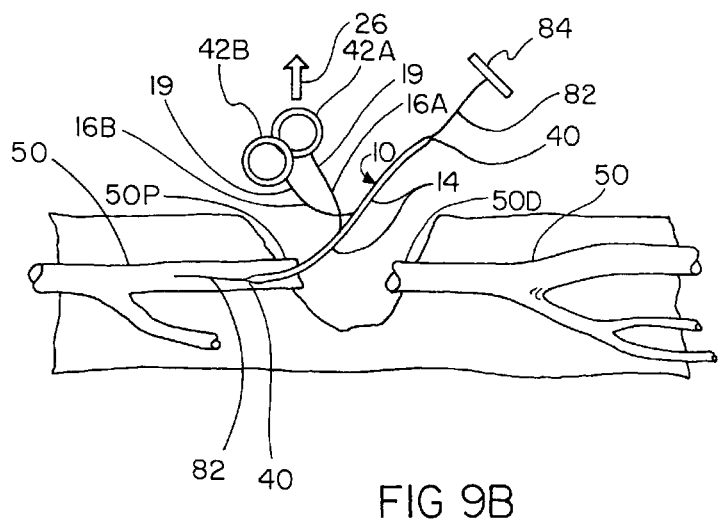
Figure 9C:
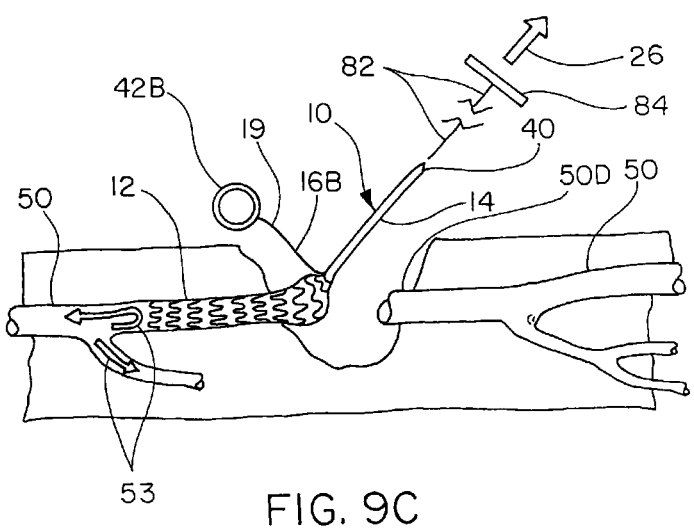

FIGS. 9A-9C are side views of an embodiment incorporating an axial stiffener that extends for the full length of the device. FIG. 9A shows as a longitudinal cross section how device 10 can be provided with an axial stiffener 82 that extends for the full length of the device. As shown, this stiffener 82 is located within the device lumen. It may alternatively be located between constraining sheath 14 and endoprosthesis 12. Stiffener 82 may take the form of a guidewire, a mandrel or rod, or a tube such as a hypotube. It may be of constant or variable stiffness along its length. Stiffener 82 may be provided with handle 84 for convenience of removability if desired.

FIGS. 9B and 9C are side views showing this embodiment as typically implanted into a body conduit. FIG. 9B describes how stiffener 82 may be used to aid in introduction of device 10 into the proximal end 50p of the body conduit 50. FIG. 9C shows how stiffener 82 may be removed from the distal end of device 10 following introduction of device 10 into the proximal end of the body conduit 50p. Stiffener 82 may be removed after insertion into proximal end of body conduit 50p, either prior to deployment or following deployment of the proximal end of device 10.

Figure 10:
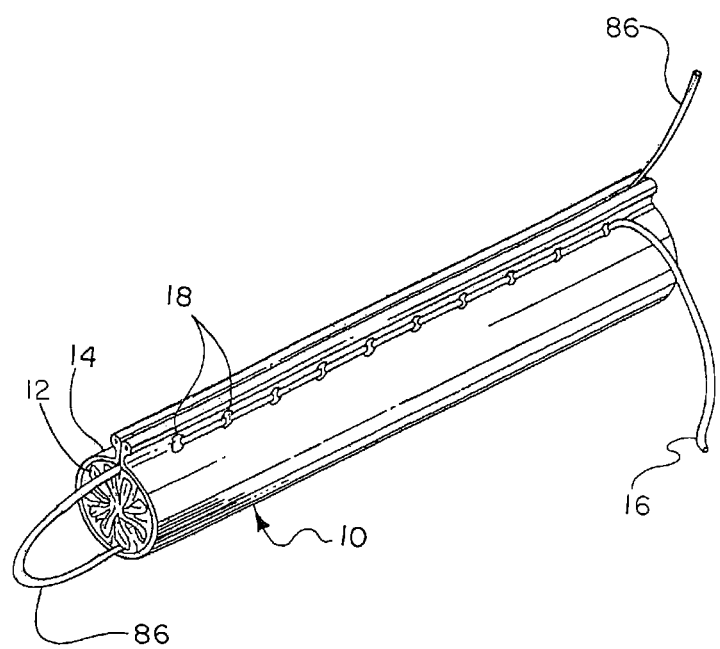
FIG. 10 is a perspective view of an alternative axial stiffener in the form of a guidewire.

FIG. 10 is a perspective view of an alternative axial stiffener in the form of a guidewire 86. In this embodiment, a moderately stiff guidewire 86 is contained within the constraining sheath 14 with the endoprosthesis 12, with the tip portion of the guidewire 86 extending beyond the end of the constrained endoprosthesis 12 and bent into a "J" form to serve as an introducer. Additionally, guidewire 86 serves as an axial stiffener. Both of these functions better enable the device 10 to be introduced into a blood vessel trauma site. If desired, the guidewire can be removed by the application of tension (indicated by arrow 26) after the assembly 10 has been introduced into the vasculature, but prior to deployment of the endoprosthesis 12.

Figure 11A:
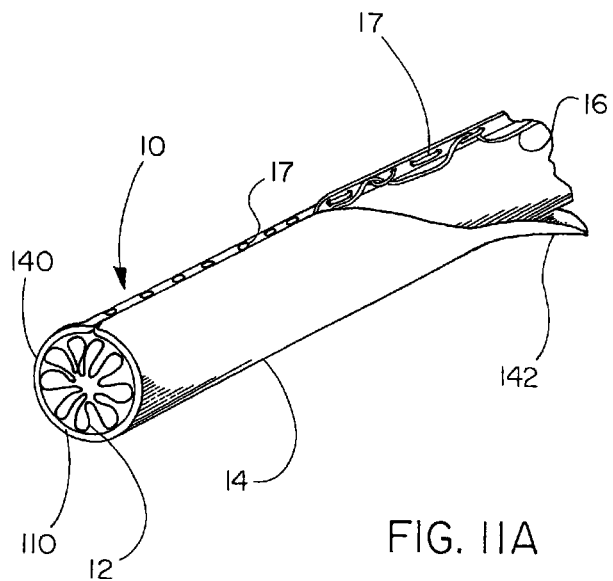
FIG. 11A is a perspective view of about one half of the length of a constrained, compacted endoprosthesis contained within an alternative constraining sheath having everted end portions.
Figure 11B:
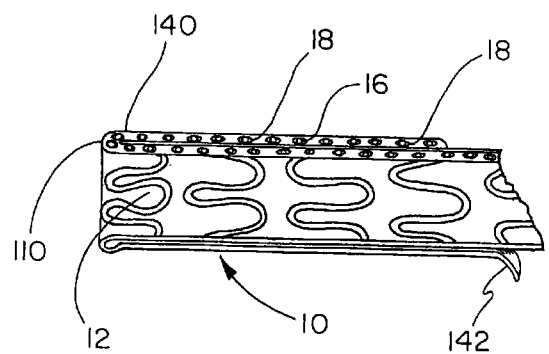
FIG. 11B is a longitudinal cross sectional view of the device shown in FIG. 11A.

FIGS. 11A and 11B show one end (e.g., the proximal end) of a constrained, compacted endoprosthesis 12 contained within an alternative constraining sheath 140. FIG. 11A is a perspective view and FIG. 11B is a longitudinal cross sectional view. In this embodiment, constraining sheath 140 is everted back over itself at the end of endoprosthesis 12. Edges of sheath 140 are again secured together by filament 16 arranged in a chain stitch 17 whereby the application of tension to the free end of filament 16 causes chain stitch 17 to come unraveled. Deployment initiates from the end of endoprosthesis 12 and progresses toward the middle of the length of endoprosthesis 12 in the similar manner as shown by FIGS. 5A-5E. Again, the opposing ends of the endoprosthesis 12 are preferably individually and independently deployable. Adjacent edges of sheath 140, secured together by chain stitch 17, thus are freed to separate and allow deployment of the endoprosthesis 12 beginning at point 110 where sheath 140 everts back over itself at the end of endoprosthesis 12. The advantage of this embodiment is that the end 142 of sheath 140 is located near the middle of the length of endoprosthesis 12. Following deployment of the proximal half of the full length of endoprosthesis 12, tension may be applied to end 142 of everted sheath 140, allowing sheath 140 to be pulled out from between the body conduit and deployed endoprosthesis 12.

Figure 12A:
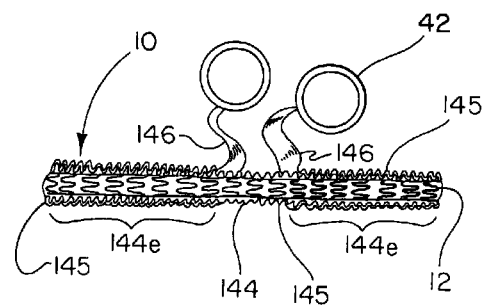
FIG. 12A is a schematic longitudinal cross sectional view of an alternative embodiment using a partially everted, corrugated constraining sheath.

FIG. 12A is a schematic longitudinal cross sectional view of another alternative embodiment using a partially everted, corrugated constraining sheath 144. Preferably, each end of the device has its own constraining sheath 144, with the two sheaths 144 meeting at about the middle of the length of the endoprosthesis 12. In this way, each end of the endoprosthesis can be separately and individually deployed. Similar to the embodiment of FIGS. 11A and 11B, a portion 144e of constraining sheath 144 is everted back over itself at both ends of compacted and constrained endoprosthesis 12, with the result that both ends 146 of constraining sheath 144 are located near the middle of the length of endoprosthesis 12. Each end 146 is affixed to a gripping means such as pull rings 42. The use of the everted sheath 144 provides a means whereby sheath 144, during deployment of endoprosthesis 12, may be removed from between the body conduit and the deployed endoprosthesis. In the embodiment shown in FIG. 12A, everted constraining sheath 144 is corrugated, with the direction of corrugations 145 running circumferentially around endoprosthesis 12. The use of a greater sheath length provided by the use of corrugations 145 reduces the required tensile force necessary to cause removal of sheath 144 and deployment of endoprosthesis 12 (due to the length of the corrugated sheath 144 being greater than the length of a similar uncorrugated sheath 14). The use of corrugations 145 also provides the sheath with increased hoop strength.

Figure 12B:
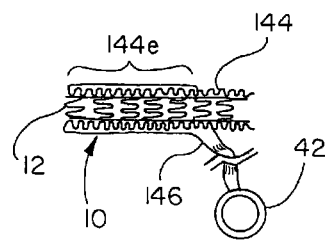
FIG. 12B is a schematic longitudinal cross section an alternative embodiment to that of FIG. 12A, wherein the everted portion of the sheath is not corrugated while the underlying portion of the sheath is corrugated.

In an alternative embodiment shown by the schematic longitudinal cross section of FIG. 12B, the everted portion 144e is not corrugated while the underlying portion of the sheath 144 is corrugated.

Figure 12C:
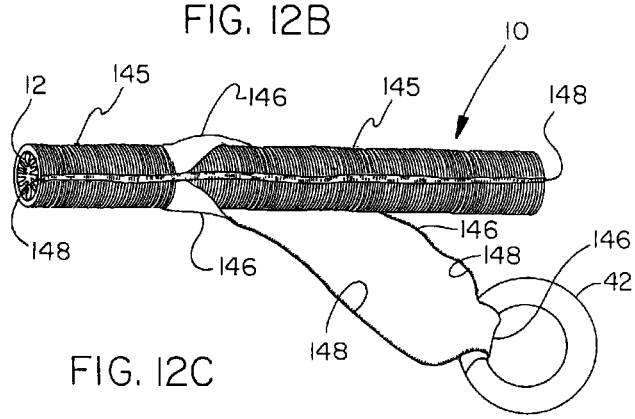
FIG. 12C shows a perspective view of about one half of the length of the embodiment of the schematic longitudinal cross sectional view of FIG. 12A.

FIG. 12C shows a perspective view of one half of the length (e.g., the proximal half) of the embodiment of the schematic cross sectional view of FIG. 12A. Corrugated and everted sheath 144 extends along the length of compacted and constrained endoprosthesis 12, with the ends of sheath 144 everted back over the middle portion of the length of sheath 144. One end 146 of sheath 144 is shown with the tubular form of the sheath 144 split lengthwise and extending to pull ring 42. Sheath 144 is thus splittable along its length by various means such as perforations provided along a line 148. Other means may also be used, including the use of thin materials for sheath 144 that have anisotropic strength properties, offering good hoop strength to the sheath but being inherently splittable along the length of the sheath.

Figure 12D:
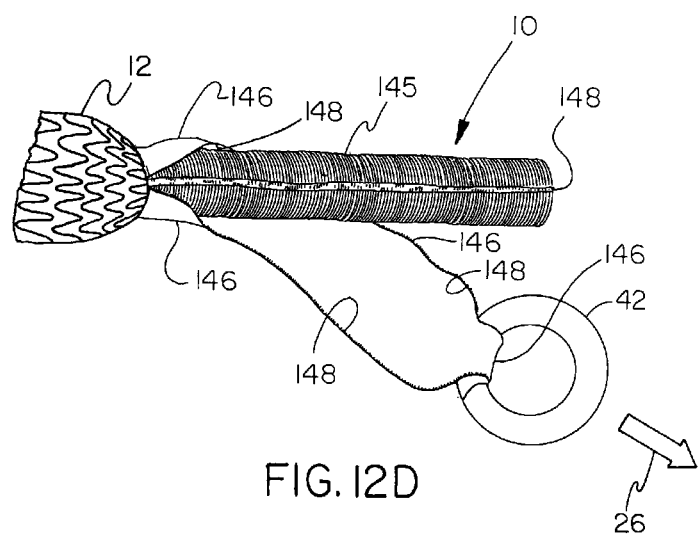
FIG. 12D shows a perspective view of initiation of deployment of the embodiment shown in FIG. 12C by the application of tension to the end of the constraining sheath via a pull ring.

FIG. 12D shows a perspective view of initiation of deployment of endoprosthesis 12 by the application of tension (shown by arrow 26) to the end 146 of sheath 144 via ring 42. This tension 26 causes end 146 to become progressively uncorrugated and causes continuing splitting of sheath 144, for example by splitting of perforation line 148. The outer, everted portion 144e of sheath 144 has been split along perforation line 148 and withdrawn, and the inner portion of sheath 144 is shown splitting as it also is withdrawn, allowing release and deployment of constrained endoprosthesis 12. Simultaneously, tension 26 results in withdrawal of sheath 144 from between the deploying endoprosthesis 12 and the adjacent wall of the body conduit into which it is being deployed.

Figure 12E:
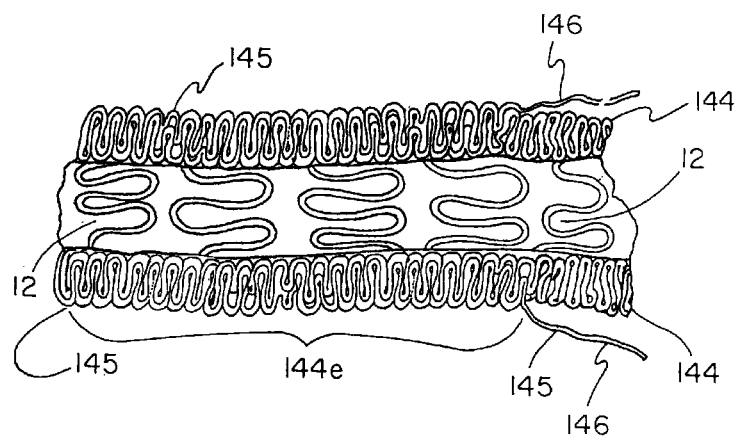
FIG. 12E shows a longitudinal cross section of one end of the embodiment described by FIGS. 12A, 12C and 12D.

FIG. 12E shows a longitudinal cross section of one end (e.g., the proximal end) of device 10 according to the embodiment described by FIGS. 12A, 12C and 12D. As shown, corrugations 145 may be non-uniform, with the corrugations 145 of the outer everted portion of sheath 144 not necessarily corresponding exactly to (and consequently not precisely matching) the corrugations of the inner portion of sheath 144.

A preferred tubular material for the partially everted, corrugated constraining sheath 144 is made from a laminated film that is a composite of fluorinated ethylene propylene (FEP) and ePTFE film wherein the FEP is applied to the ePTFE film as a discontinuous coating that allows the film to remain porous. These composite films are made as taught by U.S. Pat. No. 5,358,516 to Myers et al. A preferred ePTFE film for this laminate is taught by U.S. Pat. No. 5,814,405 to Branca.

To make a 10 cm long, partially everted, corrugated sheath, a 130 cm length of this film is paid off onto a slowly rotating stainless steel mandrel, with the 130 cm length parallel to the length of the mandrel. The mandrel is of the diameter desired for the inside diameter of the constraining sheath, with the film oriented with the FEP-coated side of the film facing away from the mandrel surface. The film has similar strength properties and tear properties in the length and width directions, so the microstructure of the ePTFE may be oriented with the length of the nodes oriented in a circumferential direction or oriented parallel to the length of the mandrel. Two layers of this film are applied, after which heat from a source such as a soldering iron, adequate to melt FEP, is applied along a line along the length of the resulting film tube. The direction of rotation of the mandrel is reversed, and two additional layers of the film are applied; the reversal of rotation results in the FEP-coated side of the film facing toward the mandrel surface. After the fourth layer is complete, the film is cut with a blade along the length of the mandrel. Finally, a temporary wrap of a tape of helically applied ePTFE film (without FEP-coating) is created over the initial four layers to hold them in place, and the film-covered mandrel is placed into a convection oven set at 320° C. for ten minutes. After this time, the mandrel is removed from the oven and allowed to cool to ambient temperature. Following cooling, the temporary overwrap of helically applied ePTFE tape is removed.

The resulting film tube had a wall thickness of about 0.020 to 0.025 mm.

Next, the resulting film tube was slid toward one end of mandrel until one end of the film tube extended a short distance (approximately 1 cm) beyond the end of the mandrel. By careful manual manipulation, the end of the tube was everted back over the portion of the tube remaining over the mandrel surface, until 10-12 cm of the end of the tube was everted over the adjacent tube portion. This was repeated for the opposite end of the film tube, resulting in the tube having two layers in each everted region. The tube was then fitted back onto the same mandrel, or optionally, another mandrel of slightly larger diameter to compensate for any diameter increase that resulted from the everting process. The tube and mandrel assembly was then placed into a suitable programmable laser cutting machine (a suitable machine is, for example, a $CO_2$ Laser Marker, model ML-G9320F available from Keyence Corporation, Woodcliff Lake N.J.). The machine had been previously programmed to cut a line of perforations for the full length of the film tube; each individual perforation was about 0.15 mm wide and of about 0.45 mm length, with adjacent perforations separated by a land of 0.2 mm length.

Following the perforation process, the resulting film tube was cut in half transversely (at the mid-point of its length) using a sharp blade, so that separate sheaths result for each end of the endoprosthesis (thereby allowing separate deployment of each end of the endoprosthesis). Next, while still on the mandrel, the sheaths are uniformly compressed in an axial direction to create the corrugations. The sheath is axially compressed until its length is 10% of its original, uncompressed length. As shown by FIG. 12E, the everted portion of the tube is corrugated simultaneously with the underlying tube portion. This figure also shows the relative non-uniformity of the corrugations.

Figure 13A:
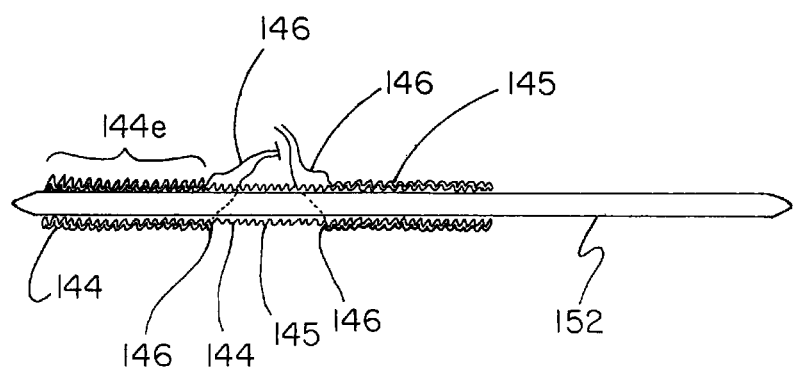
FIGS. 13A-13F show longitudinal cross sectional views of the manufacture of the partially everted, corrugated constraining sheath.

FIG. 13A shows a longitudinal cross sectional view of the manufacture of corrugated and everted constraining sheath 144. The tubing from which the sheath 144 is to be made has its ends 146 everted back over the middle portion of the tube, creating an everted portion 144e of sheath 144. The resulted everted tube 144 is fitted over a suitable mandrel 152, with the mandrel being a snug fit within the everted tube 144. The opposing ends of the everted tube 144 are then compressed axially toward each other, causing the corrugations 145 to form along the length of the sheath 144 as shown in FIG. 13A.

Figure 13B:
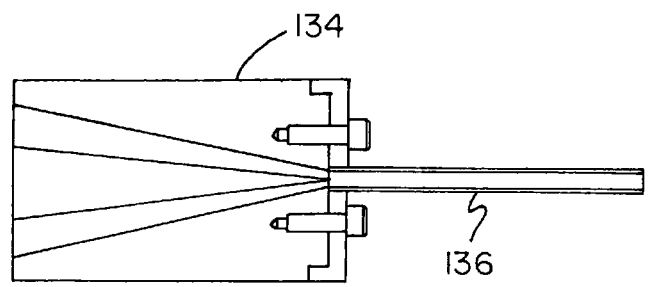

FIG. 13B shows a funnel device 132 useful for compacting a self-expanding endoprosthesis and inserting it into a constraining sheath 144. Device 132 comprises a funnel 134 of a type known in the art of manufacturing self-expandable endoprostheses. Other compaction methods may also be used, for example, iris-type compaction devices such as described by U.S. Pat. No. 6,629,350. Funnel 134 has a length of thin-wall metal tubing 136 affixed to the small end of funnel 134; the inside diameter of tubing 136 corresponds to the inside diameter of the small end of funnel 134. A suitable thin-wall tubing is a stainless steel hypotube made by Microgroup, Inc., part no. 304H11XX (Meadway Mass.).

Figure 13C:
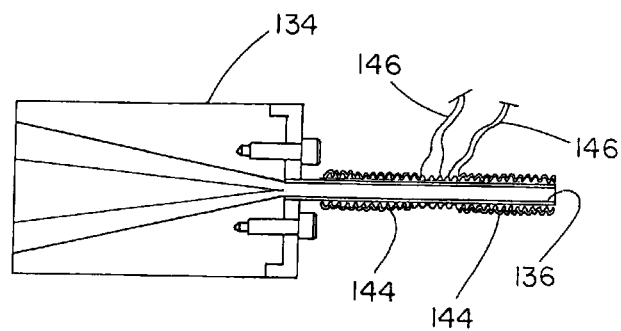
Figure 13D:
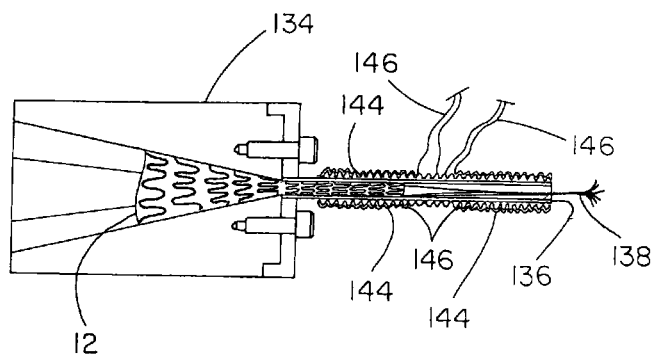
Figure 13E:
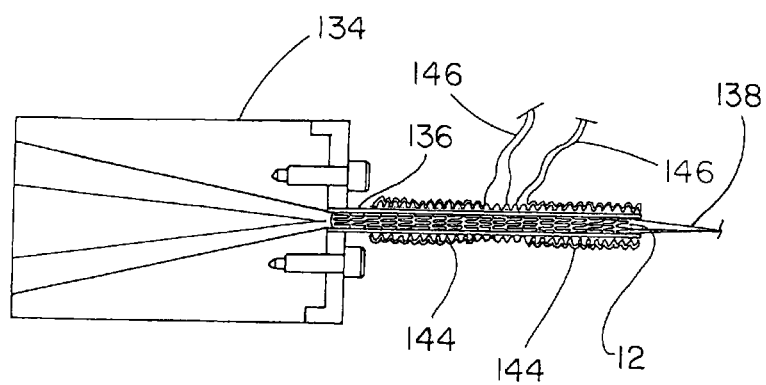
Figure 13F:
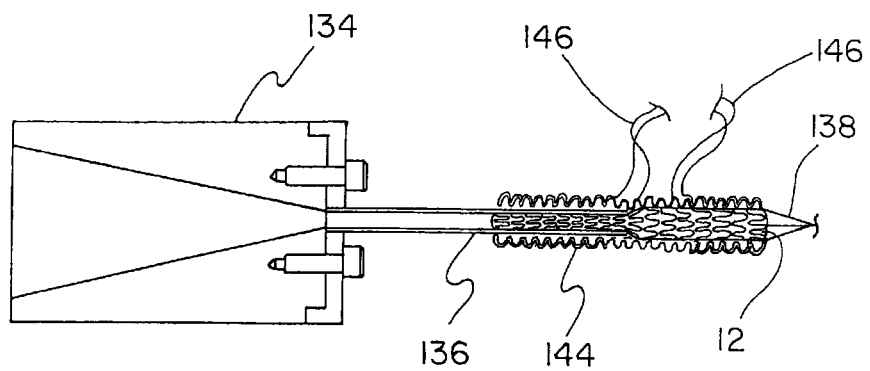

As shown by FIG. 13C, corrugated and everted sheath 144 is next fitted over the outside of tube 136. FIG. 13D shows an endoprosthesis 12 being pulled via temporary traction lines 138 into funnel 134 (nitinol stents may require simultaneous chilling with a refrigerant spray) and on into the lumen of tube 136 as endoprosthesis 12 is compacted. FIG. 13E shows the full length of compacted endoprosthesis 12 contained within the lumen of tube 136. As shown by FIG. 13F, compacted endoprosthesis is pulled out of the end of tube 136 into the lumen of constraining sheath 144, until endoprosthesis 12 is fully contained within corrugated and everted constraining sheath 144.

Figure 14:
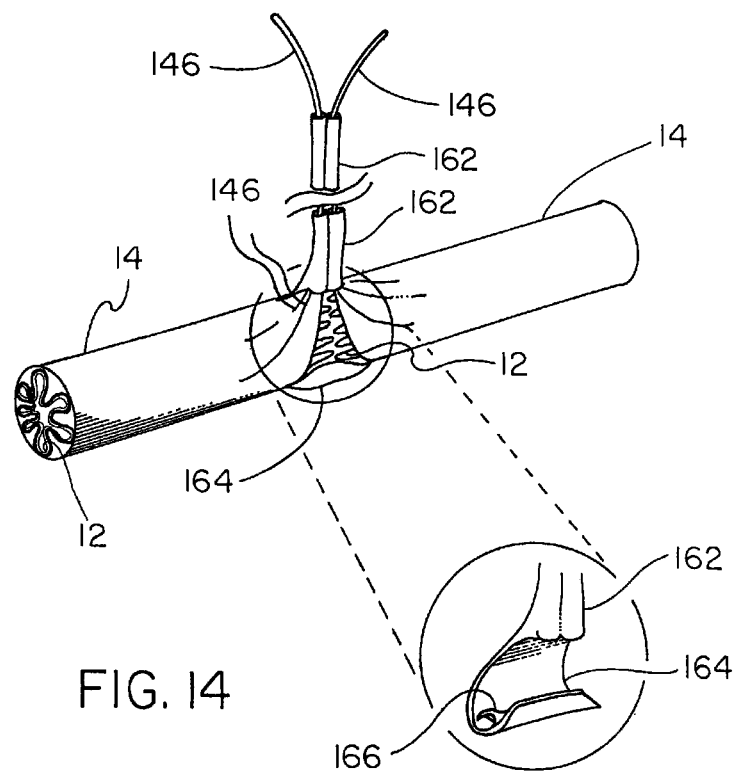
FIG. 14 shows a perspective view of an alternative embodiment wherein a guide is provided at the middle of the length of the device for facilitating the application of tension to the sheath end to initiate deployment.

FIG. 14 shows a perspective view of an alternative embodiment wherein a guide 162 is provided at the middle of the length of the device for sheath ends 146. Guide 162 is provided with a saddle 164 that holds a middle portion of endoprosthesis 12 between the two constraining sheaths 14; saddle 164 grips endoprosthesis 12 by interference. A pair of cutting blades 166 are provided in the base of saddle 164 that progressively splits each sheath 14 when tension is applied to the respective sheath end 146. As each sheath 14 splits, it is withdrawn, allowing deployment of endoprosthesis 12 beginning at the end of the endoprosthesis and progressing toward the middle, while the sheath is simultaneously withdrawn from between the endoprosthesis and the body conduit into which the prosthesis is being implanted.

Different assemblies according to the present invention were manufactured and implanted into surgically created vascular wounds created in the iliac and femoral arteries of one juvenile pig and several adult greyhound dogs, as well as a femoral vein in an adult greyhound dog. The procedures were performed under direct visualization generally as illustrated in FIGS. 5A-6D. These assemblies were based on Hemobahn® Endoprosthesis devices available from W.L. Gore & Associates, Flagstaff Ariz. These devices were compacted and constrained in ePTFE constraining sheaths having edges secured with ePTFE filaments arranged to form unravelable chain stitches. The stitch arrangement was such that each end of each assembly was individually deployable by application of tension to a pull ring fitted at one end of the ePTFE filament, resulting in deployment beginning from the end of the assembly and progressing toward the middle portion of the length of the assembly where the pull ring and filament end were located and accessible to the practitioner. Some of the constraining sheaths were provided with pointed tip portions. Some incorporated temporary axial stiffening components and some did not. Devices of 6, 7, 8 and 10 mm nominal deployed diameter were used having compacted diameters ranging from 9 to 12 French. Both fully and partially transected wounds were created. Using forceps to grip the vessel adjacent the wound opening in the vessel, these devices were inserted into the openings and deployed without undue difficulty. Deployment resulted in either complete or very substantially complete halting of blood loss and re-establishment of perfusion to the anatomy distal to the trauma site. Following complete deployment, the constraining sheaths of some of these implants were removed from the space they occupied between the deployed end of the endoprosthesis and the adjacent vessel wall by gripping an exposed portion of the constraining sheath with forceps and applying tension.

These implants were generally quickly accomplished, usually in about five minutes or less. While the devices fitted with the axial stiffeners were deemed to sometimes provide an advantage, these stiffeners were generally deemed as unnecessary to the device to enable a successful and prompt outcome.

Two additional five Hemobahn® Endoprosthesis devices were implanted in the iliac artery of two greyhound dogs. These devices had the partially everted, corrugated sheath. The sheath was deployed in one motion by pulling on its free end, one side at a time starting with the proximal side. The sheath was removed during deployment. There was little or no bleeding, which stopped by itself within 2-3 minutes. Implantation of each device lasted required less than 3 minutes. The insertion depth was about 2.5 cm proximally and 2.4 cm distally.

While particular embodiments of the present invention have been illustrated and described herein, the present invention should not be limited to such illustrations and descriptions. It should be apparent that changes and modifications may be incorporated and embodied as part of the present invention within the scope of the following claims.

We claim:

1. An intraluminal device comprising a self-expanding stent having first and second ends, said device provided with a covering over at least a portion of the stent, said first and second ends having a compacted state for insertion into a body conduit and a radially expanded state, said first end being retained in the compacted state by a first constraining sheath individually deployable from the compacted state to the expanded state by a first release filament configured to release said first constraining sheath, and said second end being retained in the compacted state by a second constraining sheath individually deployable from the compacted state to the expanded state by a second release filament configured to release said second constraining sheath, wherein deployment is initiated at the ends of said first and second sheaths and proceeds toward a middle length portion of said first and second sheaths by the individual application of tension to the first and second release filaments directly from the vicinity of the middle length portion of the device wherein the first and second ends are individually and independently deployable, and wherein, during repair of a body conduit, the first and second ends of the device may be deployed sequentially in vivo by the application of the tension individually to the first and second release filaments over any angle within a range of angles from 90 degrees to substantially parallel to a longitudinal axis of the device.

2. An intraluminal device according to claim 1 wherein said first constraining sheath comprises an end portion that extends beyond said first end of said self-expanding stent wherein said end portion is a pointed introducer with a diameter smaller than the compacted state of the self-expanding stent.

3. An intraluminal device according to claim 1 wherein said self-expanding stent has a length and said intraluminal device incorporates an axial stiffening component along at least a portion of the length of said self-expanding stent, said axial stiffening component adapted to being removed prior to radially expanding said self-expanding stent.

4. An intraluminal device according to claim 1 wherein said intraluminal device is adapted to be manually implantable under direct visualization.

5. An intraluminal device according to claim 2 wherein said second constraining sheath comprises an end portion that extends beyond said second end of said self-expanding stent wherein said end portion is a pointed introducer with a diameter smaller than the compacted state of the self-expanding stent.

6. An intraluminal device of claim 1 wherein said device comprises nitinol.

7. An intraluminal device of claim 6 wherein said device comprises ePTFE.

8. An intraluminal device of claim 1 wherein said device comprises ePTFE.

* * * * *